(12) United States Patent
Beucher et al.

(10) Patent No.: US 12,207,959 B2
(45) Date of Patent: Jan. 28, 2025

(54) RADIOLOGICAL IMAGING METHOD

(71) Applicant: EOS IMAGING, Paris (FR)

(72) Inventors: Jérôme Beucher, Esbly (FR); Pascal Desaute, Paris (FR); Khrystyna Kyrgyzov, Sceaux (FR); Audrey Lemoussu, Issy les Moulineaux (FR); Pierre Morichau-Beauchant, Paris (FR); Hamid Ouamara, Arcueil (FR)

(73) Assignee: EOS IMAGING, Paris (FR)

( * ) Notice: Subject to any disclaimer, the term of this patent is extended or adjusted under 35 U.S.C. 154(b) by 446 days.

(21) Appl. No.: 17/776,031

(22) PCT Filed: Nov. 14, 2019

(86) PCT No.: PCT/IB2019/001291
§ 371 (c)(1),
(2) Date: May 11, 2022

(87) PCT Pub. No.: WO2021/094806
PCT Pub. Date: May 20, 2021

(65) Prior Publication Data
US 2022/0386973 A1 Dec. 8, 2022

(51) Int. Cl.
*A61B 6/40* (2024.01)
*A61B 6/00* (2024.01)
(Continued)

(52) U.S. Cl.
CPC .......... *A61B 6/4014* (2013.01); *A61B 6/4241* (2013.01); *A61B 6/505* (2013.01); *A61B 6/544* (2013.01)

(58) Field of Classification Search
CPC ..... A61B 6/4014; A61B 6/4241; A61B 6/505; A61B 6/544; A61B 6/405; A61B 6/4266;
(Continued)

(56) References Cited

U.S. PATENT DOCUMENTS 5,450,462 A 9/1995 Toth et al.
8,031,831 B2 10/2011 Zou
(Continued)

FOREIGN PATENT DOCUMENTS

WO 2019008407 A1 1/2019

OTHER PUBLICATIONS

International Search Report mailed Jul. 17, 2020, in corresponding to International Application No. PCT/IB2019/001291; 3 pages.
(Continued)

*Primary Examiner* — David P Porta
*Assistant Examiner* — Meenakshi S Sahu
(74) *Attorney, Agent, or Firm* — Maier & Maier, PLLC

(57) ABSTRACT

A radiological imaging method including: 2 radiation sources with imaging directions orthogonal to each other, performing vertical scanning of a standing patient along a vertical scanning direction, wherein the radiological method includes at least one operating mode in which: a frontal scout view is made so as to identify a specific bone(s) localization within the frontal scout view, both driving current intensity and voltage intensity modulations of the frontal radiation source, depending on patient thickness and on the identified specific bone(s) localization along the vertical scanning direction, are performed simultaneously, preferably synchronously, and automatically, so as to improve a compromise between: lowering the global radiation dose received by a patient during the vertical scanning, and increasing the local image contrasts of the identified specific bone(s) localization at different imaging positions along the vertical scanning direction, for the frontal image.

24 Claims, 16 Drawing Sheets

(51) Int. Cl.
*A61B 6/42* (2024.01)
*A61B 6/50* (2024.01)

(58) Field of Classification Search
CPC ....... A61B 6/488; A61B 6/5258; A61B 6/542; A61B 6/545; A61B 6/4007; A61B 6/4258; G05B 13/027; G06N 3/02
See application file for complete search history.

(56) References Cited

U.S. PATENT DOCUMENTS

| | | |
|---|---|---|
| 2004/0086076 A1 | 5/2004 | Nagaoka et al. |
| 2005/0008219 A1* | 1/2005 | Pomero ................... G06T 7/75 382/154 |
| 2011/0026668 A1* | 2/2011 | Wu ........................ A61B 6/488 378/4 |
| 2016/0242712 A1* | 8/2016 | Jin ........................ A61B 6/5205 |
| 2018/0228011 A1 | 8/2018 | Hirayama et al. |
| 2019/0099148 A1 | 4/2019 | Rupcich et al. |
| 2019/0246999 A1 | 8/2019 | Liu et al. |
| 2019/0290234 A1 | 9/2019 | Kuwabara |
| 2022/0386972 A1* | 12/2022 | Beucher ............... A61B 6/4266 |

OTHER PUBLICATIONS

Written Opinion of the International Searching Authority mailed uly 17, 2020, in corresponding to International Application No. PCT/IB2019/001291; 7 pages.
Irrera et al., "A Landmark Detection Approach Applied to Robust Estimation of the Exposure Index in Digital Radiography", Elsevier Masson, Science Direct, IRBM, vol. 38, No. 1, Jan. 2017, pp. 42-55.

* cited by examiner

RADIOLOGICAL IMAGING METHOD

FIELD

The invention relates to radiological imaging methods, wishing to lower radiation dose received by patient, whereas still wanting to obtain patient body images of good quality.

BACKGROUND

A scanning stereo-radiographic system demonstrated interesting capabilities to make simultaneous frontal and lateral images for 3D reconstruction of skeletal anatomical parts such as the rachis or pelvis with a dose reduction up to 50 or even up to 100 compared to CT (Computed Tomography) Scan, and also a dose reduction up to 10 for single view images compared to classical CR (Computed Radiography) or DR (Direct Radiography) systems.

But this system did not have an AEC (Automatic Exposure Control), and thus the parameters of the patient scan were only manually chosen by the operator according to the evaluation he can do visually on the patient anatomy. He could only choose between three possible anatomy sizes, small, medium or large. The spectrum characteristics (kV and filter) and intensity of the X-ray beam were tuned referring to a simple table according to the choice of the protocol (full body, full spine, pelvis . . . ) and the size of the patient (small, medium or large). This system was interesting to help operator to choose the parameters, but the main drawback was linked to the only visual choice of the operator.

This drawback was also known for standard 2D radiology, and some Automatic Exposure Control (AEC) was developed to enable automatic exposure duration. This kind of AEC could stop the exposure as soon as the dose target is reached in a dosimeter cell, which is usually a radiolucent ionisation chamber, placed between the patient and the detector (film, CR, DR). This kind of AEC had also some drawbacks. A first drawback is linked again on the choice of the operator for the spectrum (kV, filter) usually selected with a crossed choice on the protocol and the size of the patient typically among 3 possibilities. A second drawback of this kind of AEC was linked to the kind of detector used to acquire the image. As long as films were used, this kind of AEC could provide correct results, because over exposure or under exposure effects are clearly visible on films which provides too light or too dark images density. Thus, the dose target of the AEC could be set to get a standard expected density for a kind of film. But when the Computed Radiography (CR) and Direct Radiography (DR) captors began to be widespread 2D detectors for radiology, other problems appeared because the operator could not anymore simply detect an over exposure or under exposure looking at the light or black image density, because these detectors and their automatic image processing can provide almost the same kind of image density whatever the dose, the only difference is the noise in the image. The operators had some difficulties to set properly the dose target according to noise in images, and the use of different kind or suppliers of CR or DR detectors models was also a cause of notable difficulties to get good results.

IEC 62494-1 proposed to use an Exposure Index (EI) which relies on the noise and thus on the Signal to Noise Ratio (SNR) of the image to define the dose target of the AEC as an Exposure Index Target (EIT). IEC 62494-1 also proposed to define a Deviation Index (DI) as the ratio of reached Exposure Index to the Exposure Index Target expressed in decibel $DI=10*\log_{10}(EI/EIT)$.

Considering a scanning radiography system, the known methods of AEC for standard 2D radiography using a dosimeter cell placed between the patient and the detector are hardly compatible for different reasons. A first reason is linked to the great difficulty or even the impossibility to change the exposure time which is linked only on the scan speed and the size of the scanned area, where for the 2D systems the AEC dosimeter cell doesn't move with respect to the patient, and therefore this static measure for 2D systems enables to stop the exposure as soon as the exposure target is reached. A second reason is the field of view of such a dosimeter for a scanning radiography system which would rely only on the very tiny part of the relevant ROI (Region of Interest) for the diagnosis in the patient body, typically only one line of the total image. The use of such a tiny part of the relevant ROI has little chance to provide a-priori information which would be required to process the parameters of the shot to get an Exposure Index in a relevant ROI close to the Exposure Index Target and to get a satisfactory Signal to Noise Ratio (SNR).

According to a first prior art outside of the technical field of radiological vertical scanning imaging, it is known a computed tomography imaging method based on a rotating radiation source emitting a very high radiation dose, in patent application US 2011/0026668, performing an helical path along an horizontal scanning direction of a patient lying on a patient bed. This radiation source is driven by both a current intensity and by a voltage intensity. Current intensity is linked to the quantity of radiation dose emitted by a radiation source in a unit of time, for example in a second. Voltage intensity is linked to the energy of each emitted photon by the radiation source. For performing such horizontal scanning of a given specific lying patient, voltage intensity is modulated so as to adapt emitted radiation dose along the horizontal scanning direction or current intensity is modulated along the horizontal scanning direction so as to adapt emitted radiation dose, which is anyway very high, and at least fifty times higher than in vertical scanning of a standing patient, to the patient thickness along the horizontal direction and so as to improve the global image contrast to the patient thickness along the horizontal direction.

In one embodiment, voltage intensity modulation is performed depending on the angular position of the radiation source along the lying patient only but not on the horizontal position of the radiation source along the lying patient, with current intensity modulation depending on the horizontal position of the radiation source along the lying patient.

In another embodiment, voltage intensity modulation is performed depending on the angular position of the radiation source along the lying patient only and on the horizontal position of the radiation source along the lying patient, but with no current intensity modulation depending on the horizontal position of the radiation source along the lying patient.

But in no embodiment of this first prior art, are simultaneously modulated both voltage intensity and current intensity, along this horizontal direction. i.e. depending on the horizontal position of the radiation source along the lying patient.

SUMMARY

The object of the present invention is to alleviate at least partly the above mentioned drawbacks.

More particularly, the invention aims to improve the compromise between:
lowering radiation dose received by patient,
and improving image quality of patient body or of patient organ.

The invention proposes to solve the problem, in vertical scanning of a standing patient, where anyway the emitted radiation dose is much lower than in computed tomography, of still reducing this emitted radiation dose, while simultaneously looking for improving image contrast differently along said vertical direction depending on patient thickness variation along said vertical scanning direction, both by modulating quantity of emitted radiation particles and by modulating intrinsic energy of each emitted radiation particle.

Thereby not only emitted radiation dose is reduced at low thickness zones of patient body and kept minimized while being maintained at a still sufficient emitted radiation dose at high thickness zones of patient body, but also intrinsic energy of each emitted particle is adapted to value of thickness in the imaged zone of patient body, thereby leading to improving not only globally emitted radiation dose, but also improving locally image contrast.

Such compromise between reduced emitted radiation dose and enhanced image contrast is possibly different at each height along said vertical scanning direction, or least changing often with variable thickness of patient body along said vertical scanning direction.

Moreover, this local image contrast is enhanced:
not globally only depending on the global thickness of the patient, as in first prior art,
but depending on both the local thickness of the patient guided on the specific bone(s) localization identified in the scout view(s).

This object is achieved with a radiological imaging method comprising: 2 radiation sources with imaging directions orthogonal to each other, one frontal radiation source and one lateral radiation source, sliding vertically so as to perform vertical scanning of a standing patient along a vertical scanning direction, wherein said radiological method comprises at least one operating mode in which: a frontal scout view is made by performing a preliminary vertical scanning of a standing patient along said vertical scanning direction by said frontal radiation source, said frontal scout view is processed to identify a specific bone(s) localization within said frontal scout view, a driving current intensity of at least said frontal radiation source is modulated along said vertical scanning direction, depending on patient thickness and on said identified specific bone(s) localization along said vertical scanning direction, a driving voltage intensity of said frontal radiation source is modulated along said vertical scanning direction, depending on patient thickness and on said identified specific bone(s) localization along said vertical scanning direction, both driving current intensity and voltage intensity modulations of said frontal radiation source are performed simultaneously, preferably synchronously, and automatically, so as to improve a compromise between: lowering the global radiation dose received by a patient during said vertical scanning, and increasing the local image contrasts of said identified specific bone(s) localization at different imaging positions along said vertical scanning direction, for the frontal image. A driving voltage intensity is synonym of a driving tension intensity.

This object is also achieved with a radiological imaging method comprising: 2 radiation sources with imaging directions orthogonal to each other, one frontal radiation source and one lateral radiation source, sliding vertically so as to perform vertical scanning of a standing patient along a vertical scanning direction, wherein said radiological method comprises at least one operating mode in which: a lateral scout view is made by performing a preliminary vertical scanning of a standing patient along said vertical scanning direction by said lateral radiation source, said lateral scout view is processed to identify a specific bone(s) localization within said lateral scout view, a driving current intensity of at least said lateral radiation source is modulated along said vertical scanning direction, depending on patient thickness and on said identified specific bone(s) localization along said vertical scanning direction, a driving voltage intensity of said lateral radiation source is modulated along said vertical scanning direction, depending on patient thickness and on said identified specific bone(s) localization along said vertical scanning direction, both driving current intensity and voltage intensity modulations of said lateral radiation source are performed simultaneously, preferably synchronously, and automatically, so as to improve a compromise between: lowering the global radiation dose received by a patient during said vertical scanning, and increasing the local image contrasts of said identified specific bone(s) localization at different imaging positions along said vertical scanning direction, for the lateral image.

This object is also achieved with a radiological imaging method comprising: 2 radiation sources with imaging directions orthogonal to each other, one frontal radiation source and one lateral radiation source, sliding vertically so as to perform vertical scanning of a standing patient along a vertical scanning direction, wherein said radiological method comprises at least one operating mode in which: frontal and lateral scout views are made by performing a preliminary vertical scanning of a standing patient along said vertical scanning direction by said frontal and lateral radiation sources, said frontal and lateral scout views are processed to identify a specific bone(s) localization within both said frontal and lateral scout views, driving current intensities of both said frontal and lateral radiation sources are modulated along said vertical scanning direction, depending on patient thickness and on said identified specific bone(s) localization along said vertical scanning direction, driving voltage intensities of both frontal and lateral radiation sources are modulated along said vertical scanning direction, depending on patient thickness and on said identified specific bone(s) localization along said vertical scanning direction, both driving current intensity and voltage intensity modulations of said frontal radiation source, as well as both driving current intensity and voltage intensity modulations of said lateral radiation source, are all performed simultaneously, preferably synchronously, and automatically, so as to improve a compromise between: lowering the global radiation dose received by a patient during said vertical scanning, and increasing the local image contrasts of said identified specific bone(s) localization at different imaging positions along said vertical scanning direction, for the frontal image and for the lateral image.

Synchronously means that:
driving current intensity and voltage intensity modulations, are, for frontal image or for lateral image, fully synchronized together. i.e. in phase with each other,
driving current intensity for frontal image is synchronized, possibly with a time shift (one of them is in advance or late of some lines in vertical direction with respect to the other one, in order to lower cross-scattering effects), with driving current intensity for lateral image, driving voltage intensity for frontal image is synchronized, possibly with a time shift (one of them is in advance or late of some lines in vertical direction with respect to the other one, in order to lower cross-scattering effects), with driving voltage intensity for lateral image.

Preferred embodiments comprise one or more of the following features, which can be taken separately or together, either in partial combination or in full combination, with any preceding object of the invention.

Preferably, said identified specific bone(s) localization includes a patient spine, preferably is a patient spine.

Indeed, patient spine is the specific bone(s) localization which is the most interesting to analyze in detail within a patient body; therefore it is used to driver both voltage intensity and current intensity modulations.

Alternatively, the specific bone(s) localization may also be a pelvis or an arm or a leg of a standing patient along a vertical scanning direction, depending on the region of interest within the part of patient body which is imaged.

Preferably, said both driving current intensity and voltage intensity modulations of said frontal radiation source are performed also so as to reach a value of signal to noise ratio which is constant and common to most of said imaging positions along said vertical scanning direction, preferably to all said imaging positions along said vertical scanning direction, for said frontal image and/or for said lateral image, but which can take two different values respectively for frontal image and for lateral image.

Preferably, for each of said frontal and/or lateral images, said signal to noise ratio value is constant and predetermined for each different patient organ to be imaged.

Preferably, for a frontal image of a patient spine, said standard signal to noise ratio value corresponds to a number of X-ray photons received per detector pixel comprised between 50 and 70, the radiological imaging method operator preferably having the possibility to deviate, via a manual command, from this standard value by at least + or −20%, more preferably by at least + or −50%, and/or for a lateral image of a patient spine, said standard signal to noise ratio value corresponds to a number of X-ray photons received per detector pixel comprised between 20 and 40, the radiological imaging method operator preferably having the possibility to deviate, via a manual command, from this standard value by at least + or −20%, more preferably by at least + or −50%.

Hence, with a constant and optimized signal to noise ratio along, or even all along, said vertical scanning direction, the local image contrasts of the identified specific bone(s) localization at different imaging positions along said vertical scanning direction are much improved, for what was indeed the region of interest within the frontal and/or lateral images.

Preferably, said frontal and/or lateral image, after having undergone at least a first step of increasing the local image contrasts of said identified specific bone(s) localization at different imaging positions along said vertical scanning direction, is normalized preferably by homogenization of regions located just outside patient body contours, in order to get rid of image artifacts coming from said driving current intensity and voltage intensity modulations.

Indeed, because of these driving current intensity and voltage intensity modulations, there were some artifacts in the frontal and/or lateral images, which were superposing some alternating waves of clear and dark grey levels on blank parts of the image (just outside the patient) or in very thin parts of the patient, rendering those images a bit less comfortable to interpret for the radiological imaging method operator, or at least needing some training on his or her side.

Preferably, said frontal and/or lateral image, after having been normalized, undergoes a contrast enhancement step.

Hence, on the one side image artifacts coming from these driving current intensity and voltage intensity modulations are cancelled whereas contrast enhancement improved by these same driving current intensity and voltage intensity modulations are not only kept but also fully taken advantage of.

Preferably, said identified specific bone(s) localization excludes metallic parts, if any, as for example metallic prosthesis of part of skeleton of patient body or as for example metallic protections put in place on patient body before performing said radiological imaging method.

Indeed, these foreign (to patient body) objects introduced within or on patient body, since being metallic and therefore stopping much more radiation, and X-ray, than the rest of patient body, can lead to some non-optimization of the emitted dose, risking to lead, for the altitudes corresponding to these foreign objects, to some over exposure or to some under exposure to emitted radiation. In modes, first where driving voltage intensity is constant, and all the more second when both driving voltage intensity and driving current intensity are constant, if metal outliers are not excluded, consequences can be worse since more or all parameters are chosen for a maximal thickness, thereby emitted a radiation dose higher or much higher than needed, what would be very detrimental to patient.

Preferably, modulations of both current intensity and voltage intensity: simultaneously increase both current intensity and voltage intensity for bigger patient thicknesses, simultaneously decrease both current intensity and voltage intensity for smaller patient thicknesses, current intensity variation rate being slower than voltage intensity variation rate.

Hence, for big patient thickness, a higher number of more energetic radiation particles go more easily through patient body despite its big thickness, without increasing emitted radiation dose too much, both thanks to higher number of emitted radiation particles and to higher energy of each emitted radiation particle, avoiding that all emitted signal is absorbed by big thickness patient body.

Whereas for small patient thickness, a higher number of less energetic radiation particles are absorbed by patient body despite its small thickness, without increasing emitted radiation dose too much, both thanks to lower number of emitted radiation particles and to lower energy of each emitted radiation particle, avoiding that all emitted signal goes through small thickness patient body.

Preferably, said current intensity modulation is maximized so as to also maximize said vertical scanning speed at a constant value.

Hence for a given emitted radiation dose, so for a given radiation dose received by standing patient during said vertical scanning, both kept at same level, the total vertical scanning time is notably reduced, having the advantage of lowering the possibility for the standing patient to move and the effects of a patient move, thereby reducing somewhat the risk of blurring and the risk of deformation of the frontal and lateral images, thereby still enhancing the signal to noise ratios of these frontal and lateral images.

Preferably, said operating mode can be either switched on or switched off manually by a radiological imaging method operator.

Hence, this very advantageous way of operating a radiological imaging apparatus is available whereas it can be cancelled if and when the operator of this radiological imaging apparatus wants to get rid of it, in order for instance to fully manually operate this radiological imaging apparatus. The radiological imaging method according to advantageous embodiments of the invention presents 3 operating modes: a full manual mode, an AEC mode without modulation, an AEC mode with modulation.

Preferably, said operating mode is dedicated to vertical scanning of large and/or obese patients.

Preferably, said operating mode is dedicated to vertical scanning of children patients.

The radiological imaging method according to the invention is all the more interesting that the thickness of the patient can be especially lower or especially higher than for an averaged size patient. This shows the capability of the radiological imaging method according to the invention to be very patient specific. Of course, the radiological imaging method according to the invention works also very well for standard sized patients.

Preferably, said current intensity modulation(s) rate do(es) not go beyond a predetermined threshold of 5 mA per millisecond, preferably a predetermined threshold of 2 mA per millisecond, more preferably a predetermined threshold of 1 mA per millisecond.

Hence, the radiological imaging method according to the invention can be performed also with relatively simple and cheap radiation sources with relatively slow current intensity driving capabilities.

Preferably, said current intensity modulation(s) at least range(s) from 20 mA to 300 mA, and preferably from 10 mA to 400 mA.

Hence, the radiological imaging method according to the invention can be performed also with relatively simple and cheap radiation sources with relatively limited ranges of current intensity driving capabilities.

Preferably, said voltage intensity modulation(s) at least range(s) from 60 kV to 100 kV, and preferably from 50 kV to 120 kV.

Hence, the radiological imaging method according to the invention can be performed also with relatively simple and cheap radiation sources with relatively limited extent of ranges of voltage intensity driving capabilities, while at the same time fully taking advantage of available ranges of voltage intensity driving capabilities.

Preferably, said vertical scanning speed value at least range(s) from 8 cm/second to 20 cm/second, and preferably from 4 cm/second to 30 cm/second.

Hence, the radiological imaging method according to the invention can be performed also with relatively simple and cheap radiation sources with relatively limited extent of ranges of vertical scanning speed capabilities, while at the same time fully taking advantage of available ranges of vertical scanning speed capabilities.

Preferably, each of said frontal and/or lateral scout view(s) is made by performing a preliminary vertical scanning of a standing patient along a vertical scanning direction with a reduced global radiation dose as compared to each of said frontal and lateral images, before making each of said frontal and lateral images.

Hence, the modulations of driving current intensity and of driving voltage intensity, as well as possibly of vertical scanning speed, depending on the thickness profile and on the specific bone(s) localization of standing patient body along the vertical scanning direction, can be determined just before performing the vertical scanning which will result in effective frontal and lateral images of standing patient body performed with a limited but full radiation dose sufficient to make high quality frontal and lateral images. The scout view(s) can be performed at the cost of quite a limited over exposure to emitted radiation.

Preferably, said reduced global radiation is less than 10% of said global radiation dose, preferably less than 5% of said global radiation dose.

Hence, the benefit is double: not only is the over exposure during scout view performance (+10% or +5%) very limited, but also it is very efficient to optimize compromise between global radiation dose received and enhancement of image contrast.

Preferably, pixels in said scout view are gathered together, preferably by zones of N×N pixels, more preferably by zones of at least 10×10 pixels, to make imaged zones, for example by zones of at least 20×20 pixels to make imaged zones.

Hence, image quality and image contrast are enhanced for the scout view, despite the very low level of emitted radiation dose used to perform this scout view.

Preferably, said images or said imaged zones are processed to identify salient points which in turn are used to compute said thickness profile and to identify said specific bone(s) localization of a standing patient along said vertical scanning direction.

Hence, it is easier and more efficient to compute said thickness profile and to identify said specific bone(s) localization of a standing patient along the vertical scanning direction, from the scout view, despite the very low level of emitted radiation dose.

Preferably, said images or said imaged zones are processed by a neural network to compute said thickness profile and to identify said specific bone(s) localization of a standing patient along said vertical scanning direction.

Hence, it is easier and more efficient to identify said specific bone(s) localization of a standing patient along the vertical scanning direction, from the scout view, despite the very low level of emitted radiation dose.

Preferably, said 2 radiation sources slide vertically so as to perform vertical scanning of a pelvis or of a spine or of a full body of a standing patient along a vertical scanning direction.

Preferably, 2 radiation detectors are respectively associated with said 2 radiations sources, said 2 radiation detectors being 2 Photon Counting Detectors (PCD) each being associated to an automatic image processing function balancing automatically image density whatever radiation dose received on the sensitive surface of said radiation detector to enhance image contrast.

Hence, over exposure or under exposure to radiation signal emitted by radiation sources is harder to be correctly assessed manually by the radiological imaging method operator. Besides. Photon Counting Detectors present improved linearity and signal to noise ratio, as compared to gaseous detectors.

Preferably, 2 radiation detectors are respectively associated with said 2 radiations sources, said 2 radiation detectors being 2 multi-energy counting detectors, preferably being 2 Energy Resolved Photon Counting Detectors (ERPCD).

Preferably, radiation is X-ray.

A standing patient or a patient in a standing position is a patient who is in a weight bearing position, contrary to a lying patient or to a patient who is in a lying position as in computed tomography. Another patient weight bearing position, alternative to patient standing position could be a patient seating position.

Further features and advantages of the invention will appear from the following description of embodiments of

DETAILED DESCRIPTION

Figure 1:
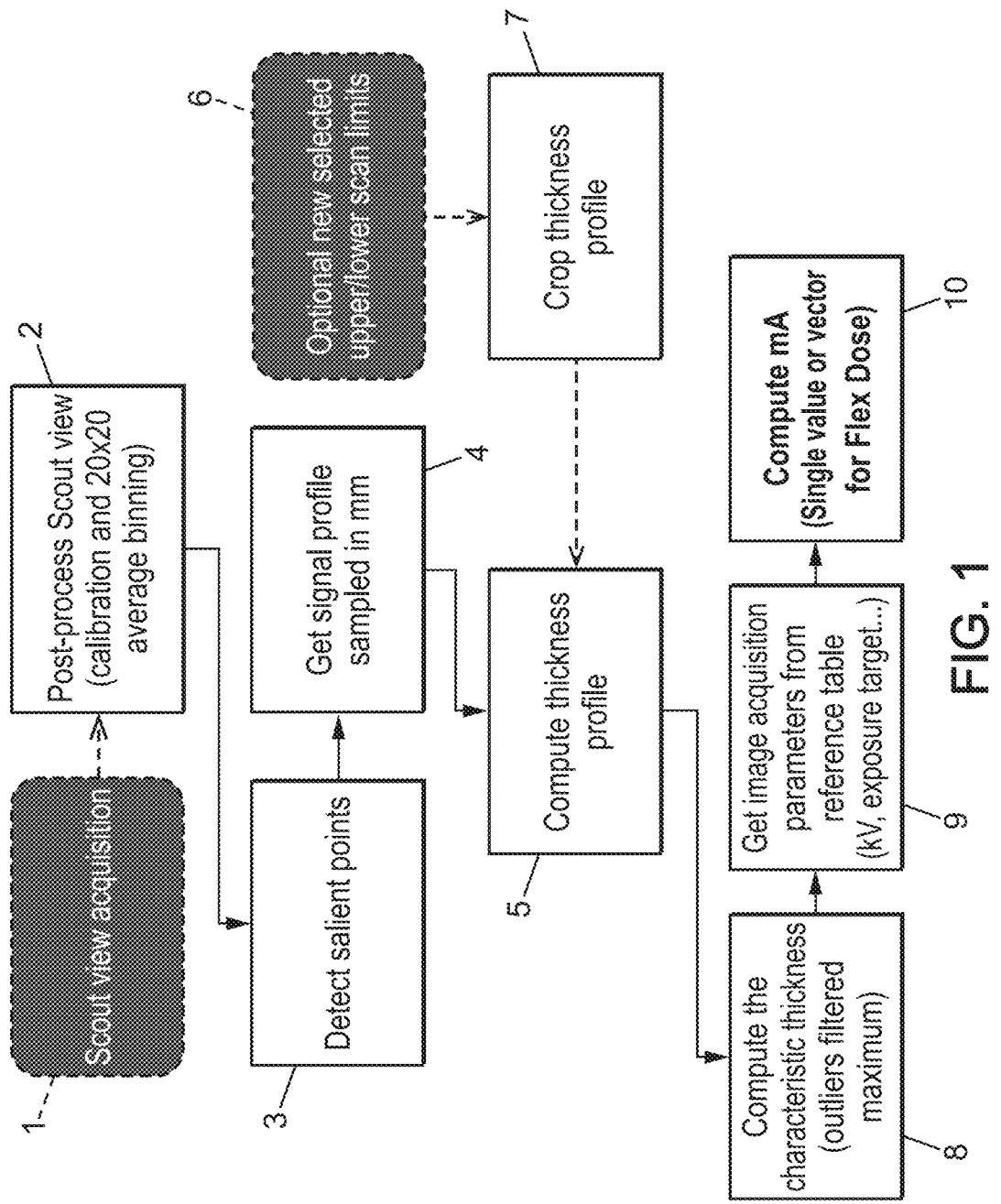
FIG. 1 shows an example of a part of the radiological imaging method according to an embodiment of the invention, dealing with computing driving current intensity modulation of radiation source.

The present invention aims at providing a solution to provide an AEC system to a scanning stereo-radiographic system, this AEC being compliant to the IEC 62494-1. This AEC system is designed to be used in the scanning stereo-radiographic system described in the applications PCT/IB2016/000273 and PCT/IB2017/000986, incorporated by reference and owned by same applicant EOS-Imaging.

In a preferred embodiment, the two detectors of this scanning stereo-radiographic system are multi-energy counting detectors, also known as Energy Resolved Photon Counting Detector (ERPCD) with at least 2 energy bins. In another embodiment, the two detectors of this scanning stereo-radiographic system are mono-energy counting detectors also known as Photon Counting Detector (PCD).

The use of the photon counting detector, in multi-energy or in mono-energy is advantageous compared to the gaseous detector for two main reasons. The first reason is the fact that the signal of the ERPCD or PCD is linear with the incoming flux and is directly equal to the number of detected photons while the signal of the gaseous detector was strongly non-linear, and this non-linearity was rather complex to model to correct it with precision. In the ERPCD and PCD a non-linear behavior still exists at high flux called the pile-up effect, but this pile-up effect can be well modeled and corrected by the image calibration software. The second reason is the fact that the ERPCD and PCD have a very stable behavior and sensitivity without the need of a new calibration during months and are not sensible to a room temperature variation, where the gaseous detector was far to be as stable and needed a daily calibration, and its behavior and sensitivity could also vary in a few minutes according to a change of room temperature. The stability of the PCD and ERPCD and the photon counting functionality enable to use directly the counting signal of incident photon in the detector to evaluate the Exposure Index and the Signal to Noise Ratio. The Signal to Noise Ratio is directly equal to the root mean square of the signal. Other kinds of energy integration detector, as the gaseous one for example, do not present this advantage and need to precise calibration to evaluate the SNR, and thus the Exposure Index.

The radiological imaging method according to embodiments of the invention is based on the use of a scout view, in mono-energy (ERPCD or PCD). As one goal of this scanning radiography system is dedicated to bones imaging for orthopedics, the scout view in that case is analyzed to find precisely the axial skeletal or bones of the selected protocol. But for some other applications, a soft tissue organ protocol as for instance the lung could be selected, and in that case the scout view is analyzed to find the organ.

The relevant ROI for the diagnosis according to the definition of IEC 62494-1 is defined by the union of a set of circular sub ROI also called 'patch' of approximately the size of a vertebrae (4-5 cm diameter), which are placed on the set of characteristics detected points or landmarks on the scout view according to a protocol specific search of bones or organs. This search of characteristics points can be embodied with two different methods: a specific salient point search algorithm or using a trained pose detection Deep Neural Network.

Then the equivalent thickness of the patient is evaluated in each patch, and some protocol of specific selection rules provides a vertical vector of equivalent thickness according to the Z (vertical) position in the patient. The equivalent thickness is evaluated in mono material PMMA [Poly (methyl methacrylate)] equivalent when mono-energy scout view is used.

The vertical equivalent thickness vector is then used to process a characteristic thickness, which is a secured detection of most probable maximum thickness. The characteristic thickness and the equivalent vector thickness are then used to process the parameters of the scan to get an Exposure index in each patch as close as possible to the Exposure Target.

The exposure parameters can be produced in a few different modes according to the choice of the operator:
- a first mode called 'constant exposure mode' provides simply the optimal constants kV, mA, filter and scan speed to use for the scan and will provide a Constant flux exposure control according to the definition of the IEC 60601-2-44;
- a second mode called 'Flex Dose' is available with two options. Both options will process a scan speed, a selected filter and a vector of temporal modulation of the exposure along the vertical axis and will provide a Z axis exposure control according to the definition of the IEC 60601-2-44.

The "Flex Dose" can be used with a first option where the voltage or tension (kV) is fixed and the current (mA) modulates along the Z axis, and in the second option both the voltage or tension (kV and the current (mA) modulate along the vertical (Z) axis. The operating mode according to the invention is this second option of the second mode called "Flex dose". This second option of the second mode called "Flex dose" is also called the AUTO mode of the scanning radiography system.

The general principle of this AUTO mode according to embodiments of the invention is different from the standard Automatic Exposure Control (AEC) used with 2D radiology detectors, for instance CR (Computed Radiography) or DR (Digital Radiography). The standard radiology AEC uses a real time dose measure, behind the patient at the 2D detector entrance level, to stop X-ray emission as soon as the target level is reached; it adjusts the exposure time based on an ionization chamber cell with a typical square shape with a side size of 5-10 cm. Generally, a standard radiology AEC device provides a choice to the operator to use one of a few different cells, for instance on the middle, on the left or on the right of the 2D detector, therefore, the exposure time is well adjusted only on the corresponding part of the cell area on the patient, and is not perfectly adjusted on the overall area of the 2D detector. Moreover, the standard radiology AEC cannot optimize all the X-ray shot parameters; it is generally required to choose the voltage (kV) manually and the filter directly or indirectly based on selection of morphology and protocol.

The AUTO mode is based on a required very low dose Scout View (also called preview or scanogram). The AEC provides a constant exposure mode and a modulation mode called 'Flex Dose' which can be respectively qualified as a Constant flux exposure control and as a Z axis exposure control. The constant flux exposure control system determines the optimum constant X-ray flux to be used over an entire scanning sequence, and the Z axis exposure control system adjusts the incident X-ray flux along the Z axis. The Z axis is vertical, as patients are in standing or seated position.

FIG. 1 shows an example of a part of the radiological imaging method according to an embodiment of the invention, dealing with computing driving current intensity modulation of radiation source.

Figure 5:
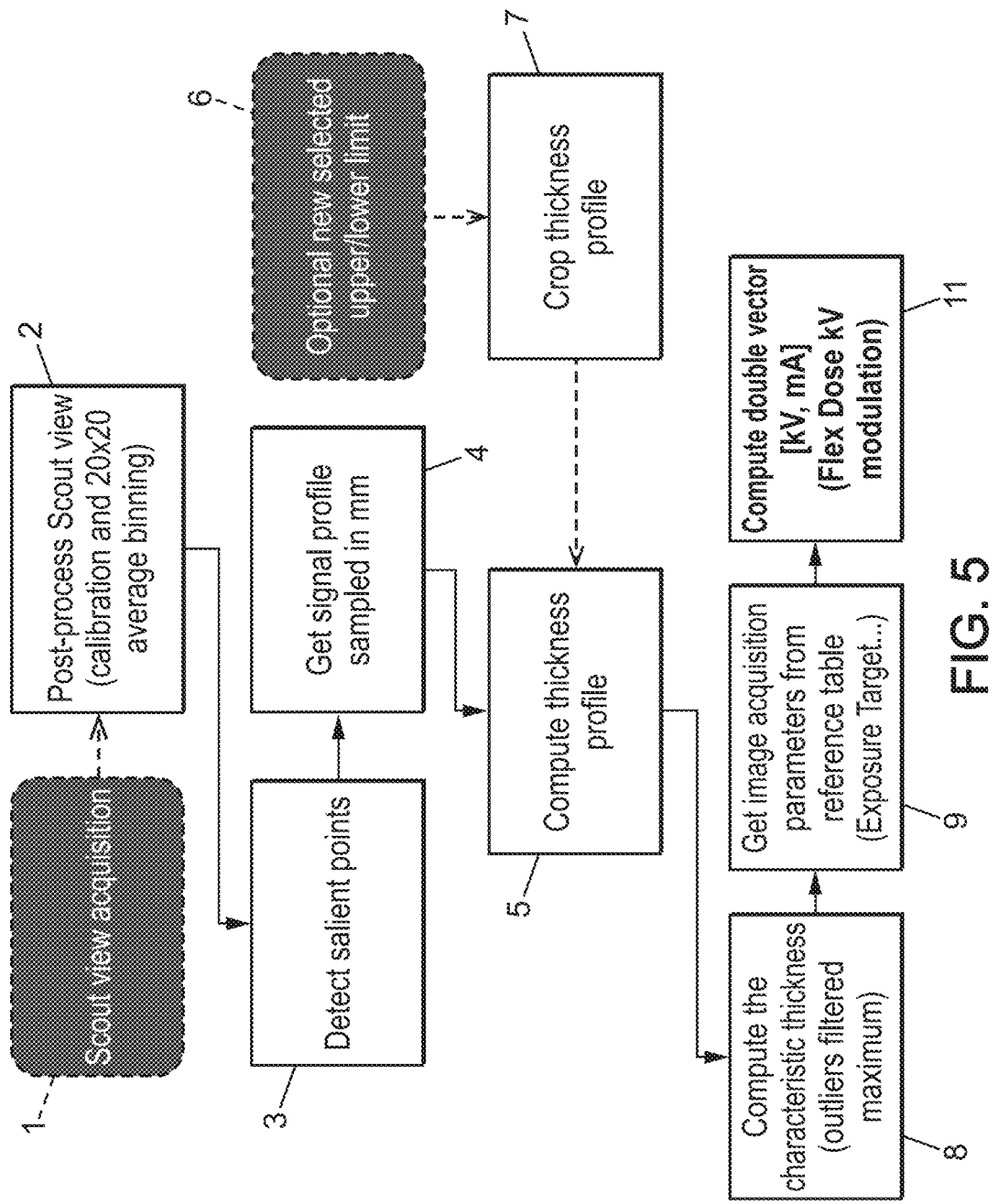
FIG. 5 shows an example of the radiological imaging method according to an embodiment of the invention, dealing with computing both driving current intensity and voltage intensity modulations of radiation source.

The radiological imaging method according to embodiments of the invention includes a method to process the current intensity and voltage intensity modulations of a radiation source along the vertical scanning direction. The FIGS. 1 and 5 present the functional block diagram of an example implementation using the salient points.

The following successive steps are performed:
In a step 1, a scout view of the standing patient is acquired with reduced radiation dose. The Scout View is required in order to use the AUTO mode and is acquired with a 0.5 mm thickness copper filter and a very low dose. The patient dose ratio between this Scout View and the main shot is less than 10% for long axis and localized protocols. This step 1 of the method is the acquisition of a scout view at reduced dose by a vertical scanning along the patient.

In a step 2, a post processing of the scout view is performed where pixels in the scout view are gathered together, preferably by zones of N×N pixels, for example by zones of at least 20×20 pixels, to make imaged zones with calibration and average binning. The Scout View was here acquired at such a low level of dose that a large binning 20×20 was applied to filter enough of the noise and get a higher level of confidence on the estimated thickness. This step 2 is the post processing of the scout view image, including the homogeneity correction using the gain calibration of the detector, and the use of a filter to improve the signal to noise ratio without introducing any bias to get a high level of confidence on the estimated thickness, for instance an average binning of 20×20 is well adapted.

Figure 14:
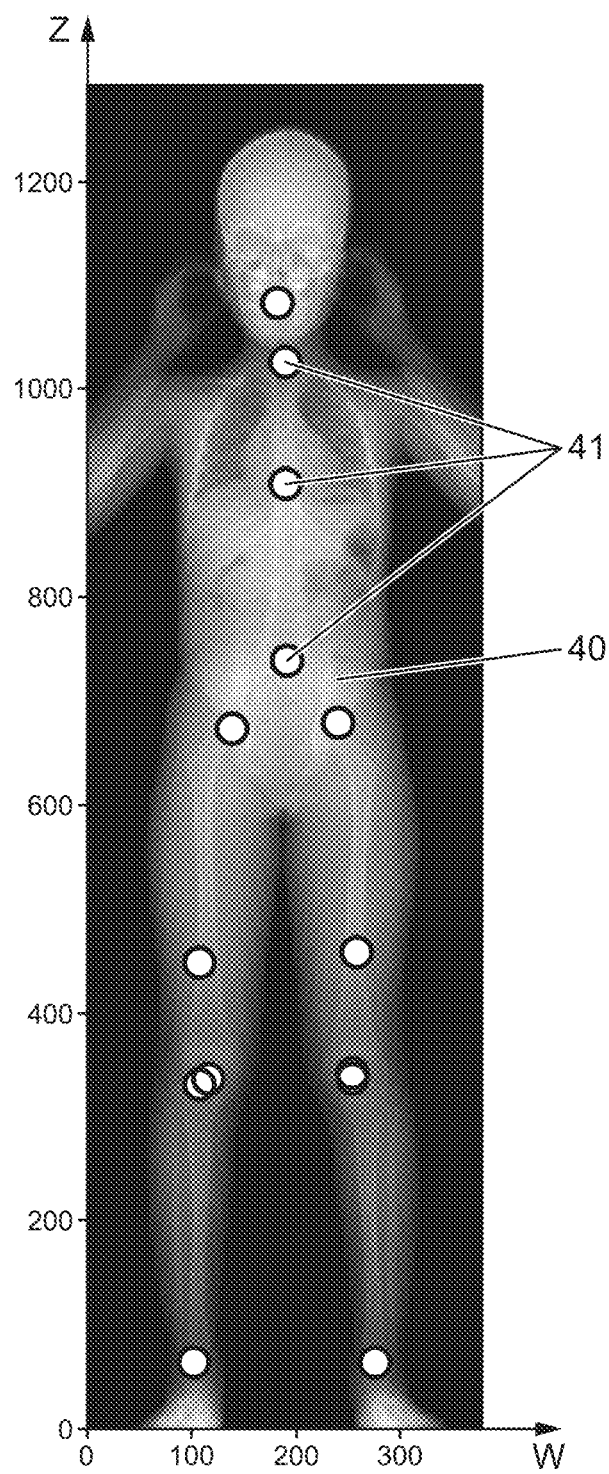
FIG. 14 shows an example of a filtered frontal scout view, after deep neural network detection step.
Figure 15:
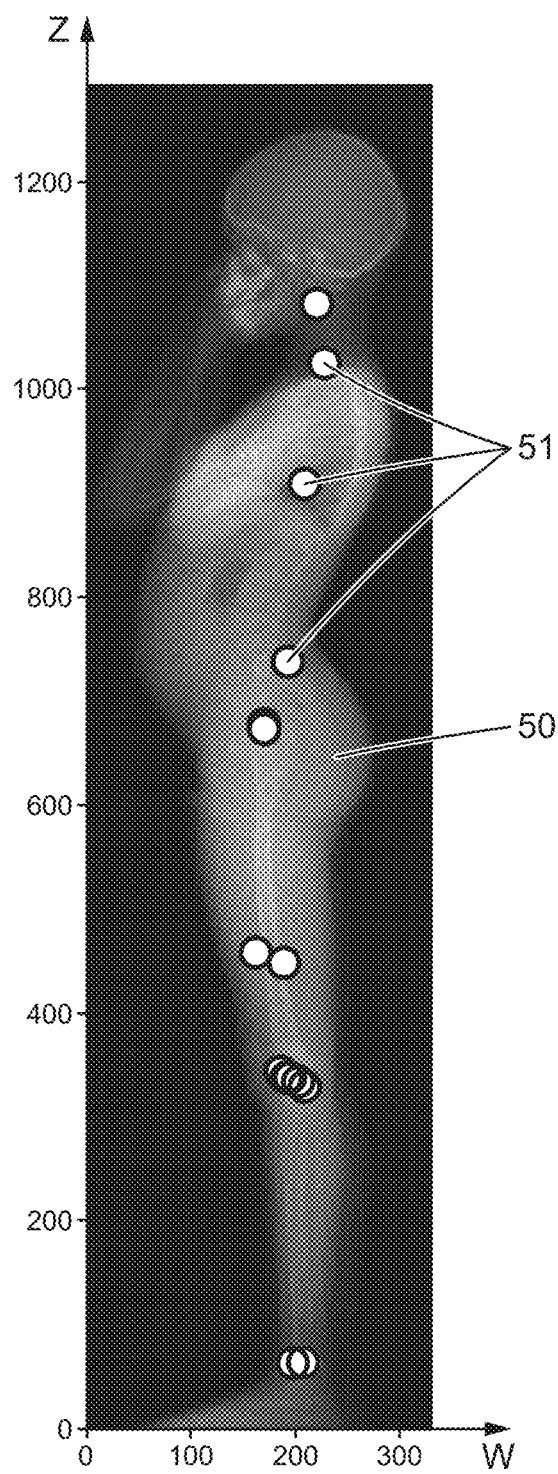
FIG. 15 shows an example of a filtered lateral scout view, after deep neural network detection step.

In a step 3, salient points are detected as will be explained in more detail with respect to FIGS. 10 to 13, where first points of higher radiation absorption are detected, and where then part of detected points are filtered out according to predetermined rules, in order to keep practically only the wished specific bones localization, for example the patient body spine, giving the salient points succession. A salient point detection algorithm developed to detect validated axial skeletal bones is applied on the binned image. The detected salient points are then selected differently in frontal and lateral images according to the patient orientation. The selected salient points mainly follow the axial skeletal composed of the lower limbs, the pelvis, the spine, the neck, and the head. A metal prosthesis or metal protection detection is also used to remove and to exclude the corresponding selected salient points in step 3 where metal detection is performed whereas in step 8 the outliers are just selected with respect to thickness. This step 3 is the detection of the specific bone(s) localization and rejection of metal parts in the scout view. As a matter of example, we use the description of the method using the salient points detection, but another implementation using a specific neural network can also be used. The salient points detection method used consists to search at a scale of a typical vertebrae size, which is around 5 cm diameter, to find a set of local maximum attenuation points in the scout view. The detected salient points are then selected differently in frontal and lateral images according to the patient orientation. The selected salient points mainly follow the axial skeletal composed of the lower limbs, the pelvis, the spine, the neck, and the head. There exists only one selected salient point at one Z altitude (at one Z position along vertical scanning direction) whereas there can be several different detected salient points at one Z altitude. The FIGS. 10 to 13 present respectively the salient points detection and selection on the frontal and lateral scout view of a patient. The left part of the FIGS. 10 to 13 present the detected salient points, and the right part of the FIGS. 10 to 13 present the selected salient points. The FIGS. 14 and 15 present an example of the skeletal detection using the neural network method, including a limited number of landmarks, applied on the same patient than for the FIGS. 10 to 13. As a matter of example, the limited number of landmarks presented in the FIGS. 14 and 15 correspond to the cervical vertebras C2 and C7, the thoracic vertebra T9, the sacrum, and on the lower limbs the left and right femoral head, ⅓ diaphysis, center of trochlea, distal tibia and proximal tibia. The selection of salient points method enables also to remove the points which are detected on metallic parts, including for example metallic prosthesis or metallic protections for breast, gonad ovary or other sensible parts of the body. The metallic parts can also be removed using the neural network method.

In a step 4, from the salient points, a signal profile is obtained as a function of vertical position expressed in mm. This step 4 is the processing of signal profile along the vertical scanning of the patient. The median value of the signal of the scout view image is processed in each circular patch centered on selected salient points and is associated to the altitude z of the corresponding salient point in the vertical scanning referential. The patch size representing an area approximately equivalent to a vertebrae size which is around 5 cm diameter. The resulting signal profile function of z is sparse, and an interpolation and extrapolation of this sparse signal profile provides a complete vertical profile sampling of signal according to the vertical altitude z on the whole height of the required vertical scanning of the patient, including some bottom and top extension of scan area for optional selection by the operator.

In a step 5, from preceding signal profile, a patient thickness profile is computed. Indeed, this step 5 is the processing of the thickness profile along the vertical scanning of the patient. The logarithm of the signal profile function of z is processed using a calibration second degree polynomial function to provide the corresponding PMMA thickness equivalent according to the equation 1:

$$t = \begin{cases} a\left[\ln\left(\frac{\text{signal}}{mAs}\right)\right]^2 + b\left[\ln\left(\frac{\text{signal}}{mAs}\right)\right] + c, \text{ if signal} > 0 \\ MaxThickness, \text{ if signal} = 0 \end{cases}$$

with $mAs=mA_{scour\ view}*time\_per\_line$ and MaxThickness=600 mm of PMMA.

The coefficients a, b and c of the polynomial are processed using a calibration.

In a step 6, optionally, new upper and/or lower scan limits can be manually selected by radiological imaging method operator. The operator can reduce or increase a little bit the height of the scan using a selection tool on the scout view images in the interface software.

In a step 7, optionally, the patient thickness profile is cropped according to preceding new upper and/or lower scan limits. The processed thickness profile function of z is then cropped according to the operator selection of the upper and lower limits of the vertical scan along the patient.

In a step 8, from preceding thickness profile, a characteristic patient thickness is computed, after filtering out outliers like metallic prosthesis or metallic protections has already be done in step 3. This step 8 is the processing of the characteristic thickness. Considering simply the maximum value of the thickness profile previously determined at the step 5 is not representative of patient's thickness when patient is sitting or with a leg on a support or with folded arms. To define a representative thickness of the patient, the derivative of the thickness profile is processed to define statistical parameters using the mean and standard deviation to remove outliers, and then the characteristic thickness is defined as the maximum thickness without considering the outliers.

In a step 9, image acquisitions parameters are taken from a reference table, according both to specific bones localization, for instance precise position of the patient spine along vertical scanning direction, and to patient thickness variation along vertical scanning direction, i.e. along height of the patient. Indeed, the processed characteristic PMMA equivalent thickness and the selected protocol are used to obtain the image acquisition parameters (kV for FIG. 1 only but not used in FIG. 5 since there is driving voltage intensity modulation, filter, scan speed) according to a reference anatomical parameters table. The step 9 is the selection in a table of the image acquisitions parameters according to the processed characteristic thickness and to the selected protocol. The parameters set comprises for instance the signal target, and the reference kV. The reference kV, mA and speed could be used to acquire the images of the patients in case the operator choose to disable the modulation, but to keep the AEC, in that case, the scan speed and the constant value of current would be processed according to the signal target and to the characteristic thickness. The reference voltage (kV) could be also used to acquire the images of the patients with the current modulation with a constant voltage (WV). Otherwise, in case the modulation is enabled, only the signal targets of the frontal and/or lateral views will be used in the following step 10 or 11. As a matter of example, the signal target for a spine exam are different for the frontal and the lateral images and are typically respectively around 60 photons/pixel for frontal view, and around 30 photons/pixel for lateral view. These values can be adjusted by the radiologist in a limited allowed range.

In a step 10, depending on the chosen operating mode, either a constant value of current intensity, or preferably a variable modulation of current intensity along the vertical direction is chosen, as a function of both the precise position of the patient spine along vertical scanning direction and the patient thickness variation along vertical scanning direction, in order to reach a constant and common signal to noise ratio along vertical scanning direction, i.e. a constant target number of X-ray photons per detector pixel along vertical scanning direction, this constant target number of X-ray photons per detector pixel along vertical scanning direction having preferably a different value for frontal image, for example 60, and for lateral image, for example 30. The final step of the AUTO mode is the processing of the current (mA) modulation vector of the image along the patient body part to scan to fit the Exposure Index Target as close as possible in every patch of the ROI. A matrix was calibrated to establish the relationship between the measured signal values as a function of a set of voltage (kV) values and PMMA equivalent thicknesses. The algorithm used to determine the current (mA) performs 2D interpolation within this matrix. Complementary and detailed explanation on the way to modulate driving current intensity can be found at FIG. 5, when describing double driving current intensity and driving voltage intensity modulation.

Figure 2:
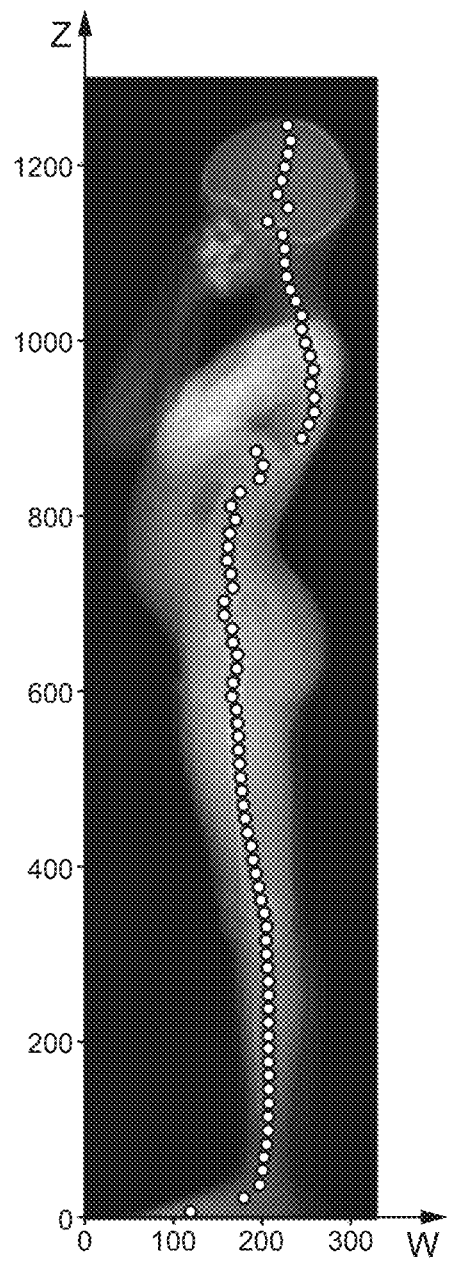
FIG. 2 shows an example of a specific bones localization, here a patient full boy including a spine continued by pelvis and leg, via salient points detection.

FIG. 2 shows an example of a specific bones localization, here a patient full boy including a spine continued by pelvis and leg, via salient points detection. The FIG. 2 presents a typical example of selected salient points on a lateral scout view.

The succession of circles follows the patient spine in a globally vertical direction. This succession of salient points SP is spotted on the lateral image of a patient body. This patient body lateral image is plotted with respect to altitude Z (height along vertical scanning direction) as a function of the patient width, patient thickness th being perpendicular to plan of figure, both altitude and width w being expressed in mm.

Figure 3:
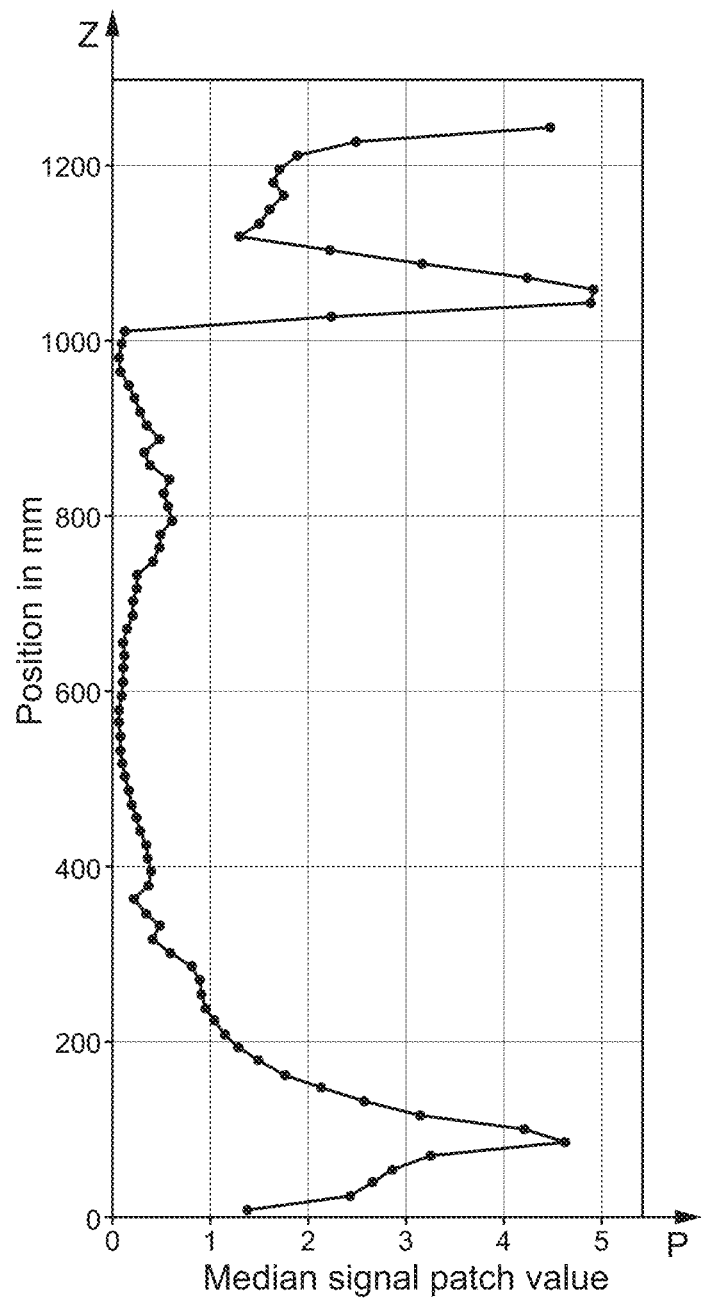
FIG. 3 shows an example of a corresponding parameter which is a median signal patch value as a function of the vertical position along the height of the patient expressed in millimeters.

FIG. 3 shows an example of a corresponding parameter P which is a median signal patch value as a function of the vertical position Z along the height of the patient expressed in millimeters. The FIG. 3 presents the corresponding fully sampled signal profile along the vertical scanning of the patient. The selected salient points are indicated in FIG. 2 on the lateral scout view by circular dots which represent the circular patch which is around 5 cm diameter.

Figure 4:
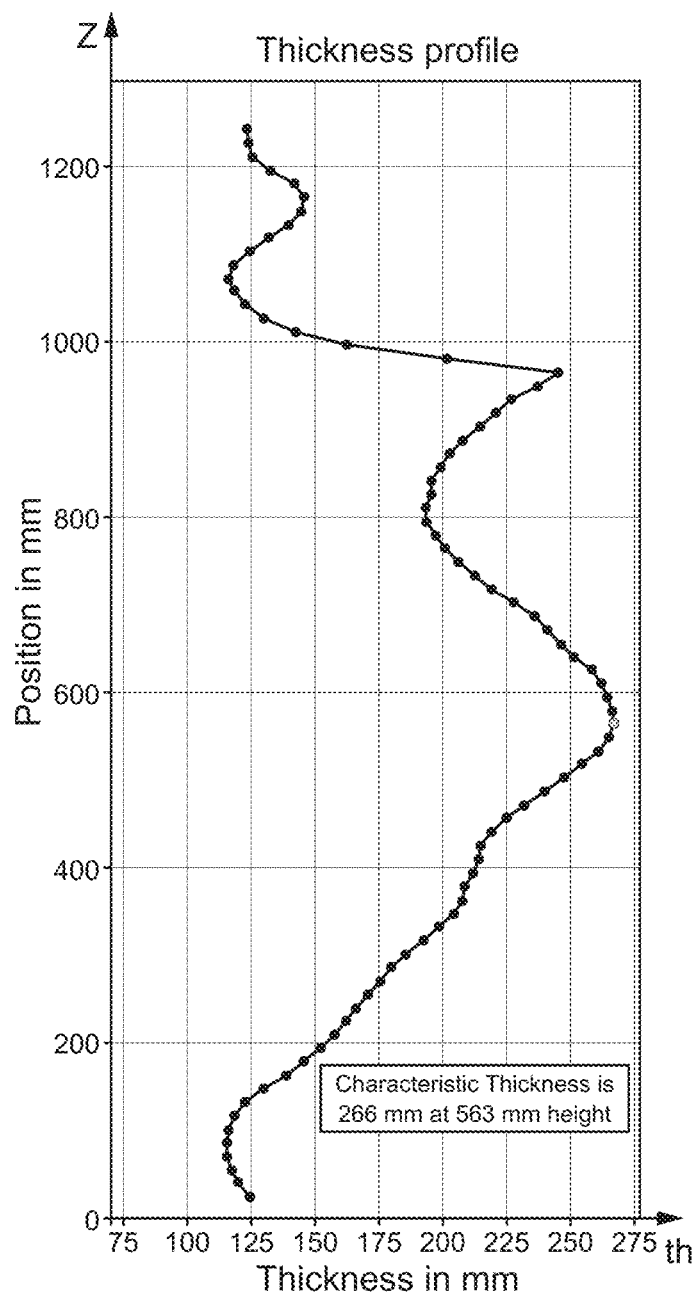
FIG. 4 shows an example of a corresponding thickness profile expressed in millimeters as a function of the vertical position along the height of the patient expressed in millimeters.

FIG. 4 shows an example of a corresponding thickness profile th expressed in millimeters as a function of the vertical position Z along the height of the patient expressed in millimeters. The FIG. 4 presents the characteristic thickness determination on the lateral profile presented in the FIG. 2.

The patient thickness profile is plotted on FIG. 4. The patient thickness th, expressed in mm, is represented as a function of the vertical position Z, also expressed in mm.

FIG. 5 shows an example of the radiological imaging method according to an embodiment of the invention, dealing with computing both driving current intensity and voltage intensity modulations of radiation source.

The same principle can be used for the "Flex Dose" with voltage (kV) modulation option to process at a first step the voltage (kV) modulation vector which improves the contrast according to thickness along the patient body part to scan, and then in a second step the current (mA) modulation to fit the Exposure Index Target as close as possible in every patch of the ROI.

There are simultaneously voltage (kV) modulation and current (mA) modulation performed in a step 11, steps 1 to 10 being similar to corresponding steps 1 to 10 previously described with respect to FIG. 1.

In this step 11, depending on the chosen operating mode, a variable modulation of voltage intensity and a variable modulation of current intensity along the vertical direction are chosen, as a function of both the precise position of the patient spine along vertical scanning direction and the patient thickness variation along vertical scanning direction so as to get an equivalent patient thickness variation along vertical scanning direction (bones attenuate more radiation, therefore they equivalent to superior thicknesses than their real thicknesses, as compared to soft tissues), in order to reach a constant and common signal to noise ratio along vertical scanning direction. i.e. a constant target number of X-ray photons per detector pixel along vertical scanning direction, this constant target number of X-ray photons per detector pixel along vertical scanning direction having preferably a different value for frontal image, for example 60, and for lateral image, for example 30.

Figure 6:
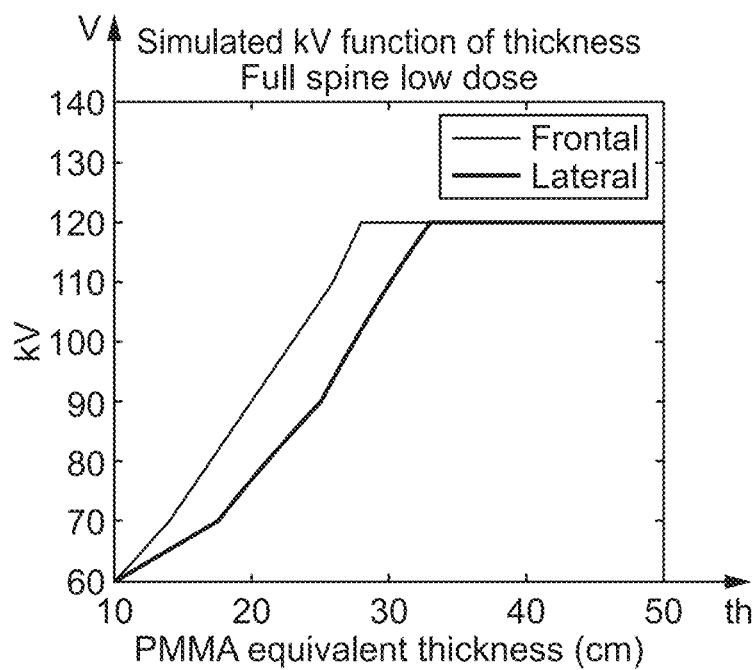
FIG. 6 shows an example of a voltage modulation expressed in kilovolts as a function of a patient equivalent thickness expressed in centimeters, respectively for the frontal image and for the lateral image.

The step 11 is the processing of the current intensity and voltage intensity modulations of a radiation source along the vertical scanning direction. The thickness profile processed at the step 5 is used to process a voltage modulation profile using a specific relation of the voltage function of the thickness, this relation can be the same or can be different for the frontal and lateral images, depending on anatomical parts. The FIG. 6 presents for instance the relations used for the full spine protocol. These voltage functions of thickness relations are determined to optimize the contrast of bones areas in the body and to minimize the dose. The contrast is known to be better at low voltage (kV) but, the use of a low voltage (kV) is not efficient looking at the useful dose which provides some signal in the detector compared to the dose received in the thick parts of a body. The choice is guided by a compromise between a better contrast leading to a lower voltage (kV) and a more efficient dose use leading to a higher voltage (kV). The processed voltage profile is used to process the optimal scan speed and the current profile. The thickness profile, the voltage profile and a 2D table representing the expected signal with respect to the voltage and to the thickness for a referenced current and scan speed is used to process the required current profile at the reference scan speed to reach the signal target. The current profile can be then adjusted proportionally to a specific scan speed. For instance, it is required to double the current profile to double the scan speed with respect to the reference scan speed. The source having a maximum output power, the maximum current profile allowed for a given scan speed can be deduced by the ratio of the maximum power and the voltage profile. The optimal scan speed is found looking at the higher allowed current profile.

The final step of the AUTO mode is the processing of the voltage (kV) modulation vector and of the current (mA) modulation vector of the image along the patient body part to scan to fit the Exposure Index Target as close as possible in every patch of the ROI. Both voltage (kV) modulation vector and of the current (mA) modulation vector can be combined together within a double voltage and intensity vector.

A matrix was calibrated to establish the relationship between the measured signal values as a function of a set of voltage (kV) values and PMMA equivalent thicknesses. The algorithm used to determine the current (mA) performs 2D interpolation within this matrix.

The voltage (kV) and current (mA) can be processed only as scalar values for the corresponding characteristic thickness in constant AEC mode, or as a one or two modulation vectors in "Flex Dose" mode to optimize the X-ray flux according to the estimated thickness of the patient along the vertical scan. The "Flex Dose" mode enables an important dose reduction for long axis protocols compared to a constant current (mA) mode, which was based only on the maximum thickness of the patient.

The overall target of AUTO mode is to reach a constant and repeatable signal level on the maximum thickness location of the patient's scanned area in constant mode, and moreover, to reach a constant and repeatable signal level all along the scanned axial skeletal of the patient and independently of the patient morphology and thickness for both modes.

Figure 7:
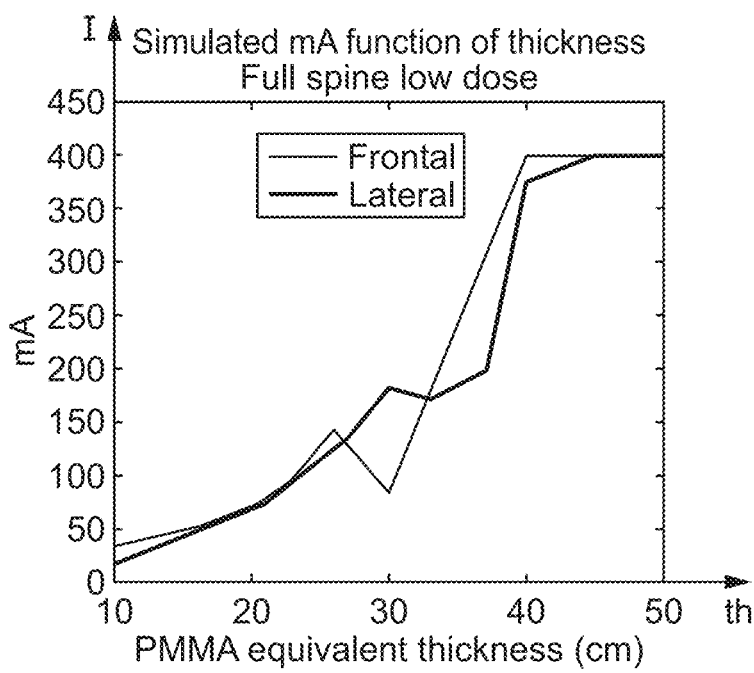
FIG. 7 shows an example of a current modulation expressed in milliamps as a function of a patient equivalent thickness expressed in centimeters, respectively for the frontal image and for the lateral image.

The FIGS. 6 and 7 present a simulation of the standard relation of the voltage (kV) and current (mA) according to the equivalent PMMA thickness for the full spine protocol in "Flex Dose" mode.

FIG. 6 shows an example of a voltage modulation V expressed in kilovolts as a function of a patient equivalent thickness th expressed in centimeters, respectively for the frontal image and for the lateral image. For the frontal curve F, voltage increases regularly from about 60 kV to about 120 kV, for equivalent patient thicknesses ranging from about 10 cm to about just below than 30 cm, and then is kept constant at about 120 kV from about just below 30 cm to 40 cm or 50 cm.

For the lateral curve L, voltage increases regularly from about 60 kV to about 120 kV, for equivalent patient thicknesses ranging from about 10 cm to about just above 30 cm, and then is kept constant at about 120 kV from about just below 30 cm to 40 cm or 50 cm. Increase of F curve is steeper than increase of L curve.

FIG. 7 shows an example of a current modulation I expressed in milliamps as a function of a patient equivalent thickness th expressed in centimeters, respectively for the frontal image and for the lateral image.

For the frontal curve F, current increases regularly from about 30 mA to about 400 mA, for equivalent patient thicknesses ranging from about 10 cm to about 40 cm, and then is kept constant at about 400 mA from about 40 cm to about 50 cm.

For the lateral curve L, current increases regularly from about 20 mA to about 400 mA, for equivalent patient thicknesses ranging from about 10 cm to about 40 cm, and then is kept constant at about 400 mA from about 40 cm to about 50 cm. Increase of F curve is similar, on the average, to increase of L curve.

Figure 8:
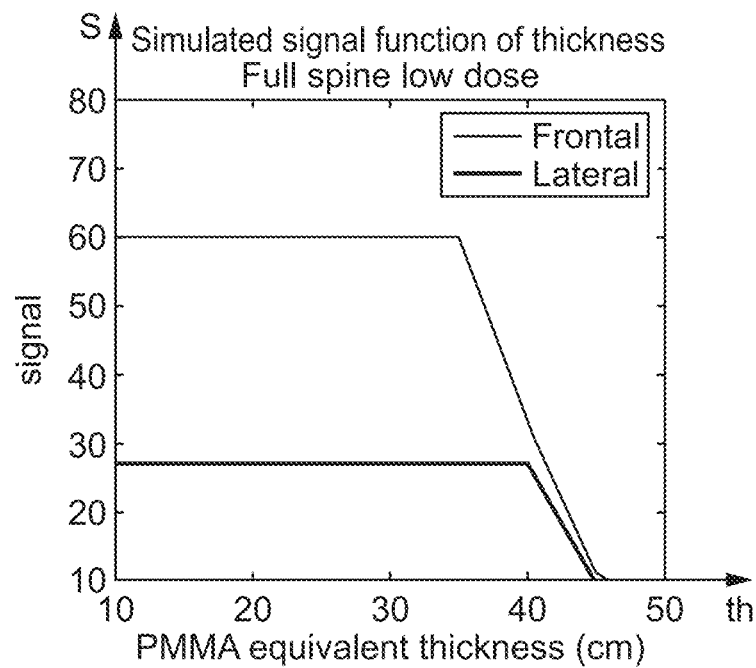
FIG. 8 shows an example of obtained numbers of X-ray photons per detector pixel (representative of signal to noise ratios) as a function of a patient equivalent thickness expressed in centimeters, respectively for the frontal image and for the lateral image.

FIG. 8 shows an example of obtained numbers S of X-ray photons per detector pixel (representative of signal to noise ratios) as a function of a patient equivalent thickness th expressed in centimeters respectively for the frontal image and for the lateral image.

For the frontal curve F, the number of X-ray photons per detector pixel is rather constant at about 60, for equivalent patient thicknesses ranging from about 10 cm to about 35 cm, and then decreases abruptly from about 60 to about 10, for equivalent patient thicknesses ranging from about 35 cm to about 50 cm.

For the lateral curve L, the number of X-ray photons per detector pixel is rather constant at about 27, for equivalent patient thicknesses ranging from about 10 cm to about 40 cm, and then decreases abruptly from about 27 to about 10, for equivalent patient thicknesses ranging from about 40 cm to about 50 cm. Decrease steepness of F curve is similar to decrease steepness of L curve, but extends on a larger equivalent patient thicknesses range.

Figure 9:
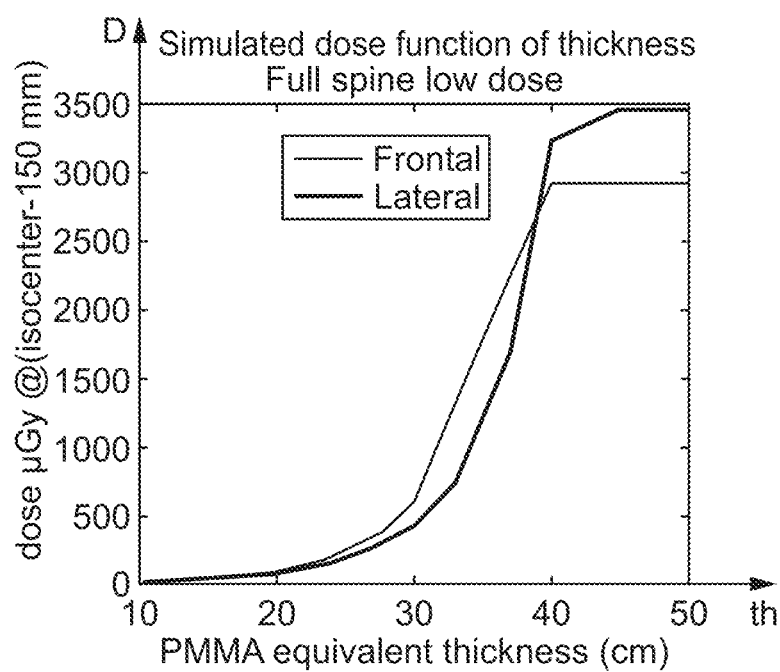
FIG. 9 shows an example of radiation dose received by patient in μGy (microgray), as a function of a patient equivalent thickness expressed in centimeters, respectively for the frontal image and for the lateral image.

FIG. 9 shows an example of radiation dose D received by patient in µGy, as a function of a patient equivalent thickness th expressed in centimeters respectively for the frontal image and for the lateral image.

For the frontal curve F, the radiation dose received by patient increases first slowly from about none to about 500 micrograys, for equivalent patient thicknesses ranging from about 10 cm to about 30 cm, then increases much more abruptly from about 500 micrograys to about 3000 micrograys, for equivalent patient thicknesses ranging from about 30 cm to about 40 cm, and afterwards remains roughly constant at about 3000 micrograys, for equivalent patient thicknesses ranging from about 40 cm to about 50 cm.

For the lateral curve L, the radiation dose received by patient increases first slowly from about none to about 700 micrograys, for equivalent patient thicknesses ranging from about 10 cm to about 33 cm, then increases much more abruptly from about 700 micrograys to about 3500 micrograys, for equivalent patient thicknesses ranging from about 33 cm to about 40 cm, and afterwards remains roughly constant at about 3500 micrograys, for equivalent patient thicknesses ranging from about 40 cm to about 50 cm. L curve increases more slowly than F curve in first phase of slow increase, but then L curve increases more rapidly than F curve in second phase of abrupt (or quick) increase.

The "Flex Dose" mode enables to get better results than the Constant mode on Exposure Index accuracy compared to Exposure Index Target on every patch, and especially on long axis protocols. Moreover, the voltage (kV) modulation and current (mA) modulation option compared to the current (mA) modulation only option of the "Flex Dose" mode enables to get a better accuracy on the Exposure Index compared to the Exposure Index Target because it enables to get faster modulation than the mA only (limited to 1 mA/ms against 5 kV/ms, with ms for millisecond), thus is better to fit closely the fast changes of thickness in the patient body, and it also enables to overcome some generator current (mA) modulation limits of the X-ray tube, for instance the current (mA) modulation currently is usually limited to 10 mA minimum. Another improvement of the simultaneous use of voltage (kV) modulation is to optimize also the contrast to the local thickness at the same time as to fit the Exposure Index Target.

On all FIGS. 10 to 18, the scale along horizontal and vertical axis are in mm, after scout view image has been binned (which means each zone of 20×20 original square pixels has been gathered in a new pixel), for scout view, frontal and lateral images taken after scout view having no such binning.

FIG. 10 to FIG. 13 show frontal and lateral images using a step of salient points detection, both before and after filtering in order to focus on the patient spine (or on the patient spine continued by one of his or her leg) and to exclude other bones, in order to enhance image contrast on the zone of interest which is here the patient spine.

This filtering step aims at selecting only salient points which are located most probably on axial skeleton, here on spine and on one leg continuing the spine.

Figure 10:
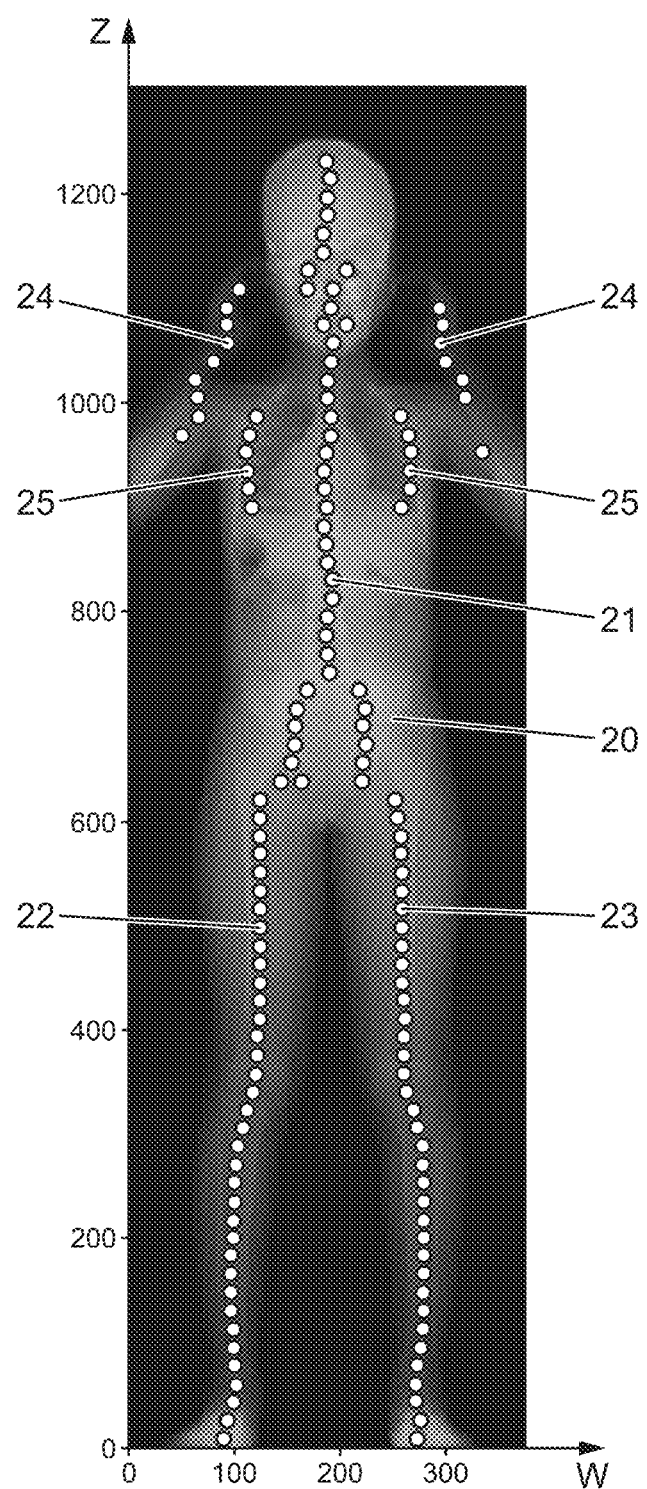
FIG. 10 shows an example of a filtered frontal scout view, after salient points detection step, but before salient points filtering step.

FIG. 10 shows an example of a filtered frontal scout view, after salient points detection step, but before salient points filtering step. This patient body image is plotted with respect to altitude Z (height along vertical scanning direction) as a function of the patient width, patient thickness th being perpendicular to plan of figure, both altitude and width w being expressed in mm.

Figure 11:
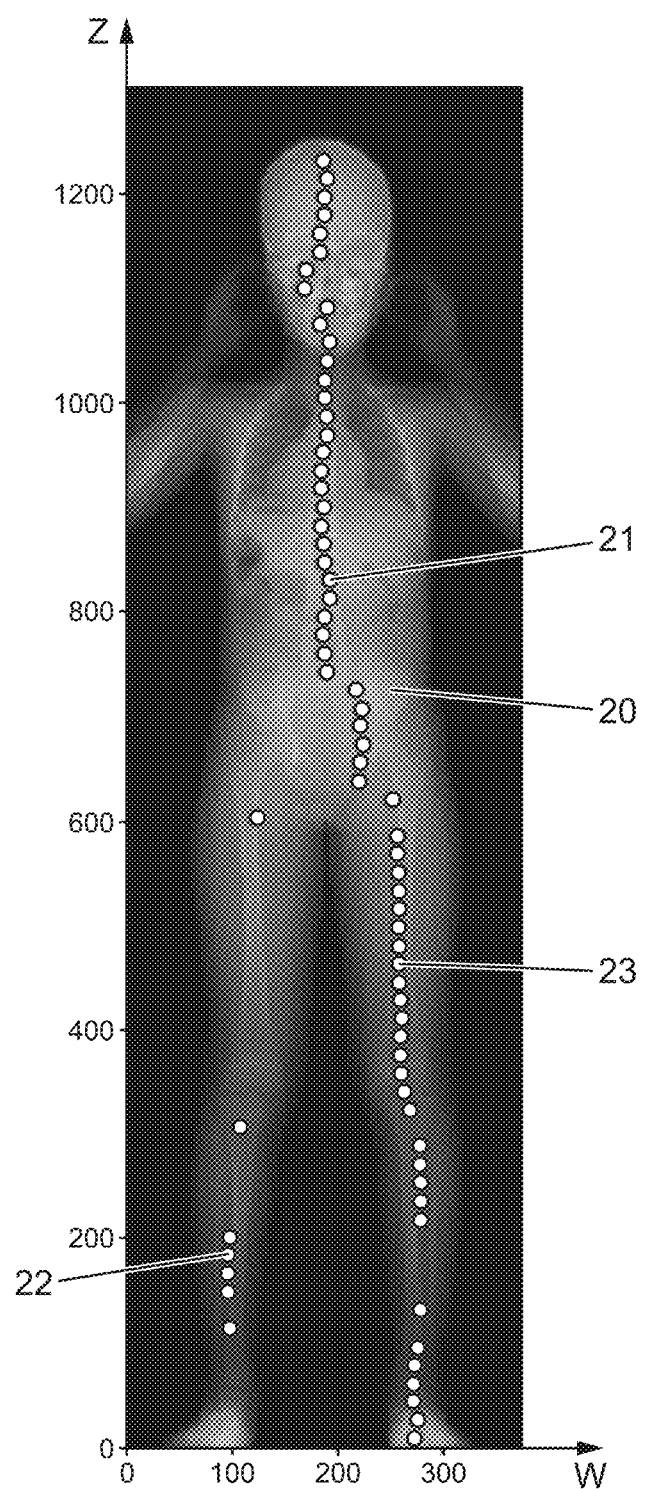
FIG. 11 shows an example of a filtered frontal scout view, after salient points detection step and after salient points filtering step.

FIG. 11 shows an example of a filtered frontal scout view, after salient points detection step and after salient points filtering step. This patient body image is plotted with respect to altitude Z (height along vertical scanning direction) as a function of the patient width, patient thickness th being perpendicular to plan of figure, both altitude and width w being expressed in mm.

Bones 21 to 25 are spotted within patient 20. Patient 20 is plotted with respect to his or her height Z expressed in mm with respect to his or her width also expressed in mm.

Rules for frontal image filtering step are the following ones:
  For each Z (vertical position) value, the salient point with maximal thickness is chosen,
  Metal parts are excluded even if they correspond to a salient point with maximal thickness (metal parts correspond to very steep attenuation or absorption changes with their vicinity within patient body).
When filtering has been performed within patient 20 frontal image:
  Only remain spine 21, left leg 23 and a small part of right leg 22,
  Whereas arms 24, shoulders 25 and most of right leg 22 have been filtered and thereby excluded.

Figure 12:
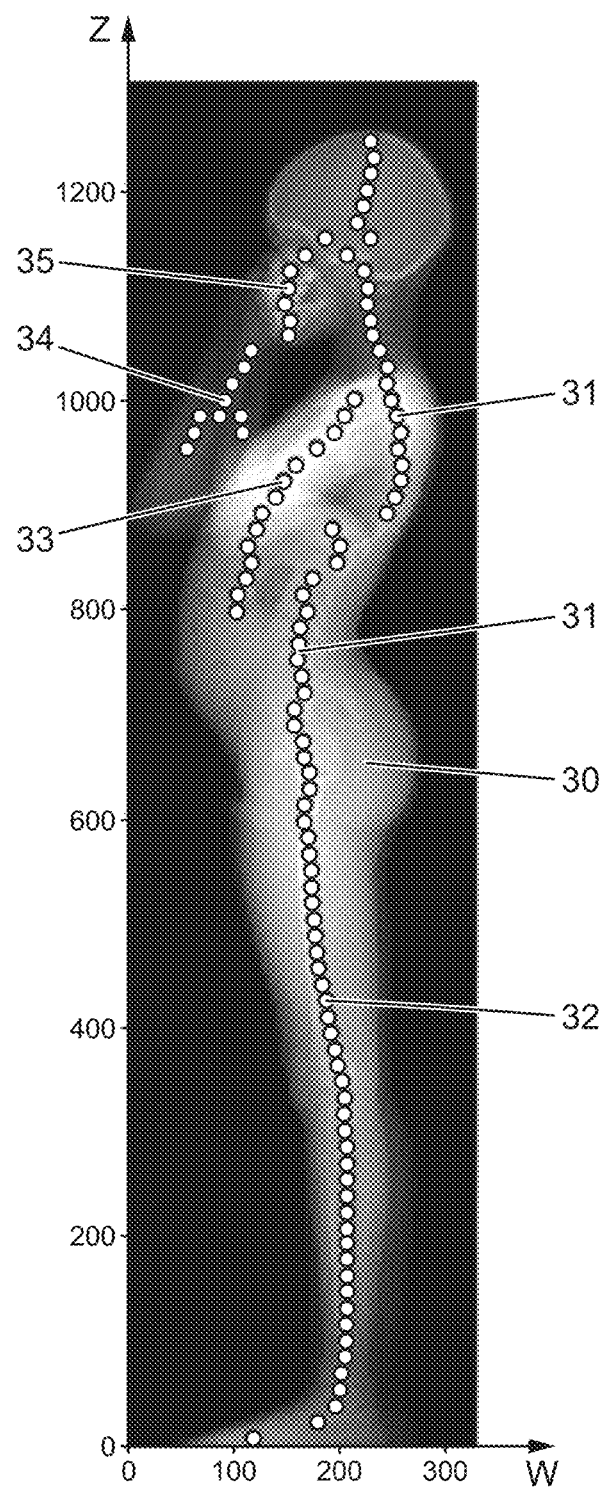
FIG. 12 shows an example of a filtered lateral scout view, after salient points detection step, but before salient points filtering step.

FIG. 12 shows an example of a filtered lateral scout view, after salient points detection step, but before salient points filtering step. This patient body image is plotted with respect to altitude Z (height along vertical scanning direction) as a function of the patient width, patient thickness th being perpendicular to plan of figure, both altitude and width w being expressed in mm.

Figure 13:
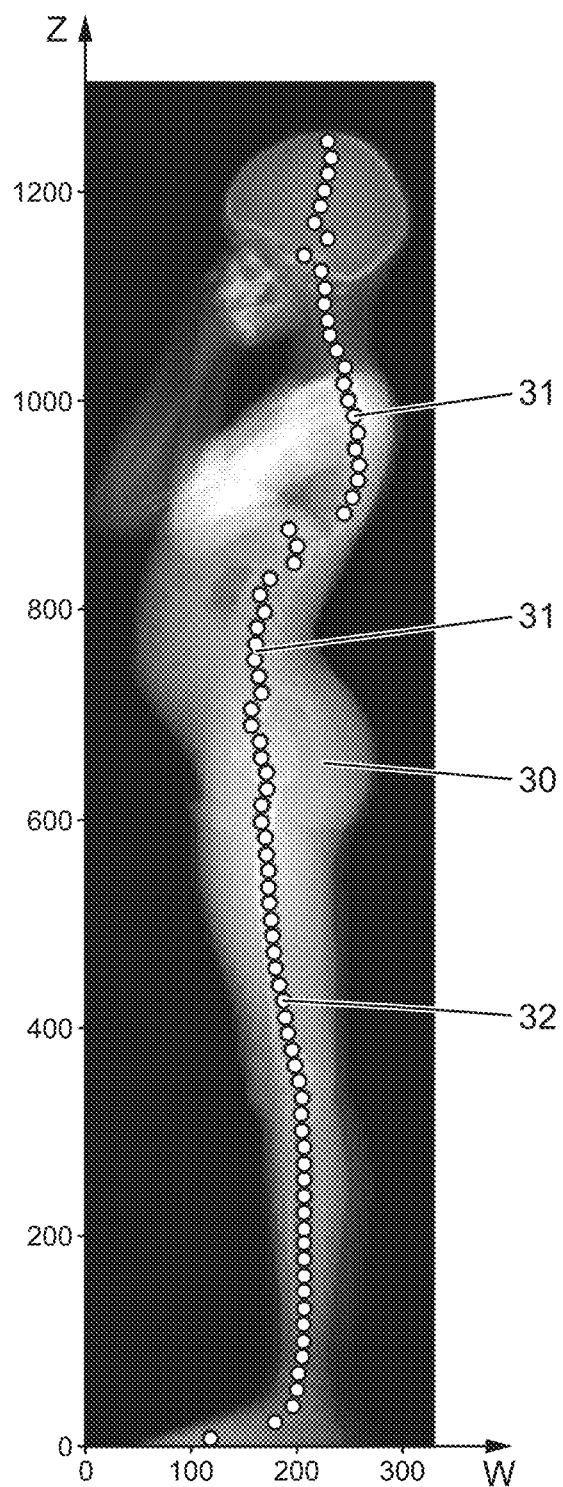
FIG. 13 shows an example of a filtered lateral scout view, after salient points detection step and after salient points filtering step.

FIG. 13 shows an example of a filtered lateral scout view, after salient points detection step and after salient points filtering step. This patient body image is plotted with respect to altitude Z (height along vertical scanning direction) as a function of the patient width, patient thickness th being perpendicular to plan of figure, both altitude and width w being expressed in mm.

Bones 31 to 35 are spotted within patient 30. Patient 30 is plotted with respect to his or her height Z expressed in mm and with respect to his or her width also expressed in mm.

Rules for lateral image filtering step are the following ones:
  For each Z (vertical position) value, the salient point closest to patient back is chosen (corresponding here to the salient point the more on the right of the lateral image since patient is looking toward left side, but it would correspond to the salient point the more on the left of the lateral image if patient were looking toward right side),
  Metal parts are excluded even if they correspond to a salient point with maximal thickness (metal parts correspond to very steep attenuation or absorption changes with their vicinity within patient body),
  Still exclude some isolated salient points too close to the patient back, further than patient spine toward right side of lateral image, for example some isolated salient points lost in soft tissues zones like in buttocks or in flesh portion of back.
When filtering has been performed within patient 30 lateral image:
  Only remain spine 31 and left leg 32,
  Whereas arms 33 and 34, as well as jaws 25, have been filtered and thereby excluded.

Voltage intensity and current intensity modulations may be calibrated.

First, an image with fixed current value is taken, with a stepped voltage modulation, covering voltage available range (50-140 kV).

Then, obtained image is corrected by calibration software homogenizing detector and correcting its non-linearity.

Then, signal is measured for each voltage step value, value of these steps comes from a feedback measure file of the generator after radiation emission.

Then, by interpolation, an evolution curve f(kV) is determined which gives a signal as the product of the evolution curve f(kV) by the mA (and also for a given reference acquisition frequency of detector). f can be for example expressed as a number of received X-ray photons per pixel detector divided by the current in vertical axis and as a voltage in horizontal axis, and also can be a straight line on a range 40-120 number of photons by mA vertically and on a range 80-130 kV horizontally and having started more progressively and smoothly on a range 10-40 number of photons by mA vertically and on a range 50-80 kV horizontally.

A specific image, either frontal or lateral, may also be corrected:
  A profile of driving voltage intensity and current intensity modulations is calculated from the scout view.
  Then an image is acquired with the calculated modulations profile.
  Then, obtained image is corrected by calibration software homogenizing detector and correcting its non-linearity.
  Then, use is made of the feedback measure file of the generator after radiation emission, in order to identify at each line j of taken image the value effectively sent by the generator of voltage kV(j) and current mA(j) at this line j.
  Then the image is normalized: signal of each line j of taken image is divided by the product [f(kV(j))*mA(j)].

FIG. 14 shows an example of a filtered frontal scout view, after deep neural network detection step. This patient body image is plotted with respect to altitude Z (height along vertical scanning direction) as a function of the patient width, patient thickness th being perpendicular to plan of figure, both altitude and width w being expressed in mm.

There is a patient 40 represented on a frontal image with landmarks 41 plotted by the deep neural network.

FIG. 15 shows an example of a filtered lateral scout view, after deep neural network detection step. This patient body image is plotted with respect to altitude Z (height along vertical scanning direction) as a function of the patient width, patient thickness th being perpendicular to plan of figure, both altitude and width w being expressed in mm.

There is a patient 50 represented on a lateral image with landmarks 51 plotted by the deep neural network.

Figure 16:
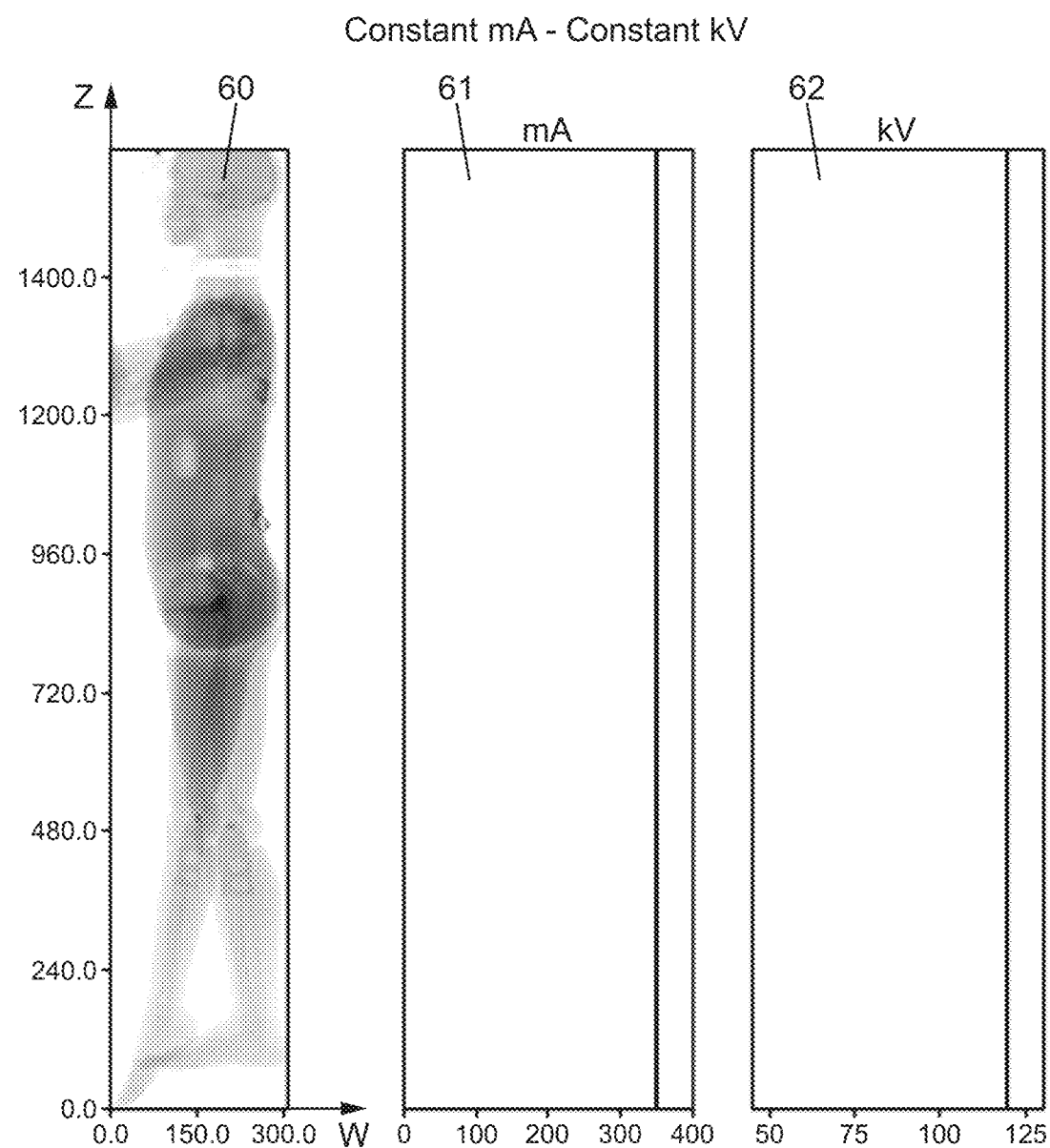
FIG. 16 shows an example of lateral image, of constant driving current intensity and of constant driving voltage intensity, in a constant current and voltage mode.

FIG. 16 shows an example of lateral image, of constant driving current intensity and of constant driving voltage intensity, in a constant current and voltage mode. The FIG. 16 presents the lateral scan of an anthropomorphic phantom in the case of the modulation is disabled.

A patient 60 is represented on a lateral image. This patient body image is plotted with respect to altitude Z (height along vertical scanning direction) as a function of the patient width, patient thickness th being perpendicular to plan of figure, both altitude and width w being expressed in mm. There is a constant driving current intensity 61 all along the vertical scanning direction Z, for example at about 350 mA. There is a constant driving voltage intensity 62 all along the vertical scanning direction Z, for example at about 120 kV. Patient 60 lateral image is of average quality.

Figure 17:
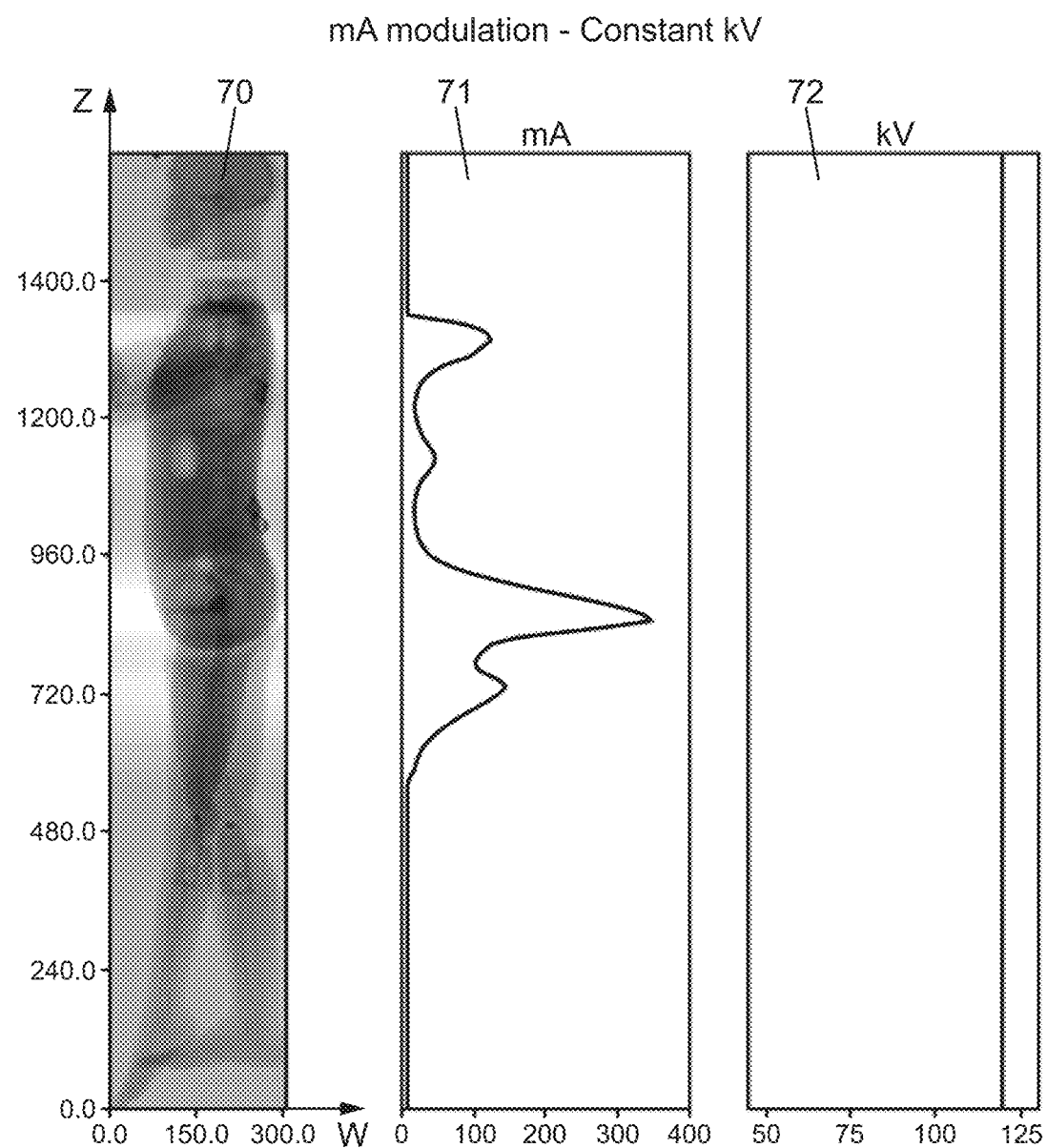
FIG. 17 shows an example of lateral image, of modulated driving current intensity and of constant driving voltage intensity, in a modulated current and constant voltage mode.

FIG. 17 shows an example of lateral image, of modulated driving current intensity and of constant driving voltage intensity, in a modulated current and constant voltage mode. The FIG. 17 presents the lateral scan of the anthropomorphic phantom in the case of the modulation is enabled but with a fixed voltage (kV).

A patient 70 is represented on a lateral image. This patient body image is plotted with respect to altitude Z (height along vertical scanning direction) as a function of the patient width, patient thickness th being perpendicular to plan of figure, both altitude and width w being expressed in mm. There is a driving current intensity modulation 71 all along the vertical scanning direction Z, for example varying between about 10 mA and about 350 mA. There is a constant driving voltage intensity 72 all along the vertical scanning direction Z, for example at about 120 kV. Patient 70 lateral image is of notably similar quality than patient 60 lateral image, but taken with a lower radiation dose and adjusted to get the right level of signal at each position along vertical scanning direction.

Figure 18:
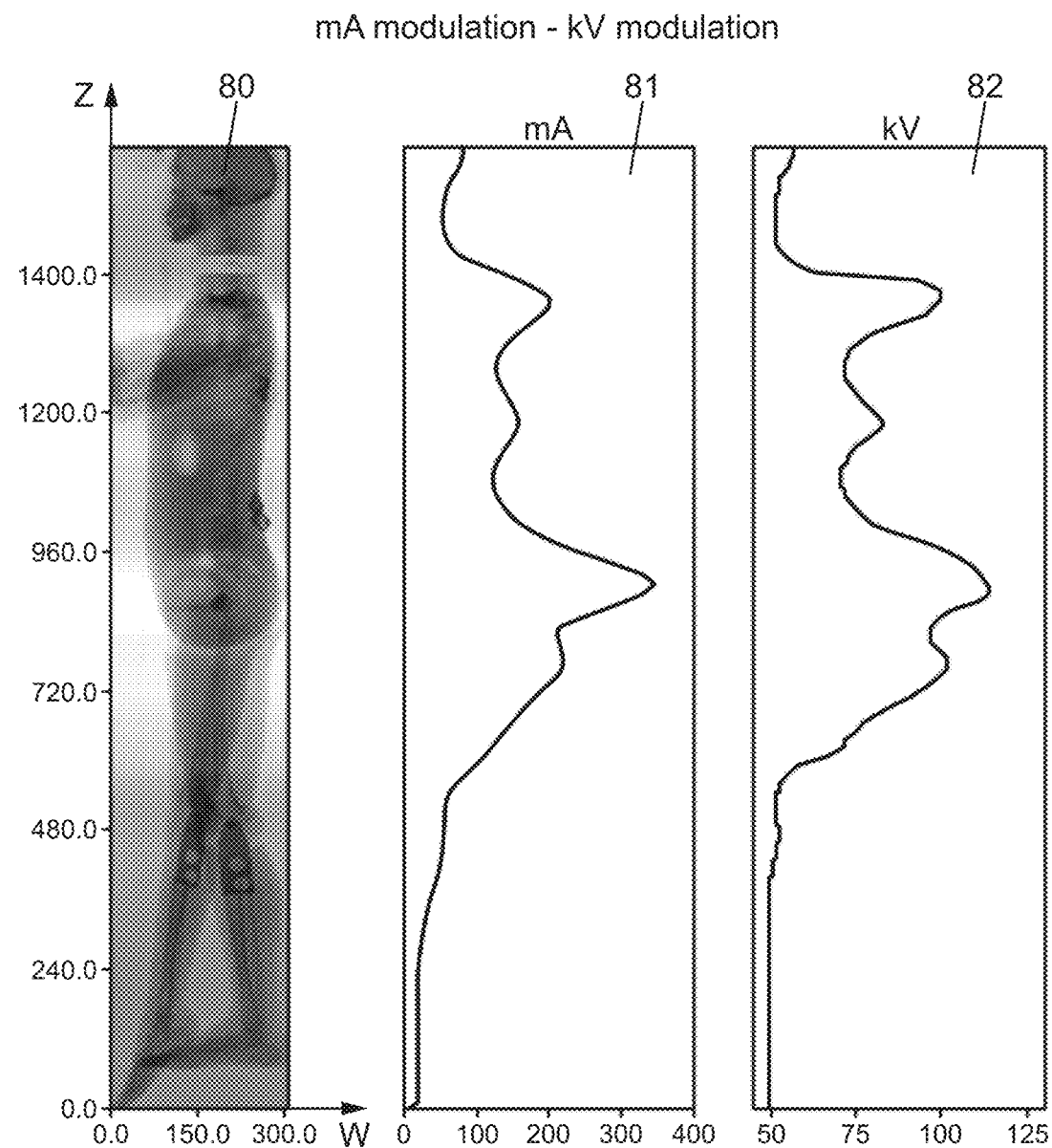
FIG. 18 shows an example of lateral image, of modulated driving current intensity and of modulated driving voltage intensity, in a double modulated current and voltage mode.

FIG. 18 shows an example of lateral image, of modulated driving current intensity and of modulated driving voltage intensity, in a double modulated current and voltage mode. The FIG. 18 presents the lateral scan of the anthropomorphic phantom in the case of the modulation is enabled for voltage and current.

A patient 80 is represented on a lateral image. This patient body image is plotted with respect to altitude Z (height along vertical scanning direction) as a function of the patient width, patient thickness th being perpendicular to plan of figure, both altitude and width w being expressed in mm. There is a driving current intensity modulation 81 all along the vertical scanning direction Z, for example varying between about 10 mA and about 350 mA. There is also a driving voltage intensity modulation 82 all along the vertical scanning direction Z, for example varying between about 50 kV and about 120 kV. Patient 80 lateral image is of notably better quality than patient 70 lateral image and of much better quality than patient 60 lateral image, and patient 80 lateral image is also taken with a lower radiation dose than patient 60 lateral image.

One can see in the images presented in the FIGS. 17 and 18 compared to the one from the FIG. 16 that the blank or void part of the image outside the patient is modulated correspondingly to the modulation profiles applied. The image is then corrected by the normalization with the excepted signal without attenuation to remove this modulation of the blank part in images, to avoid compromising the radiologist analysis of the image. The demodulated image follows then a standard contrast enhancement process before the presentation to the radiologist.

Figure 19:
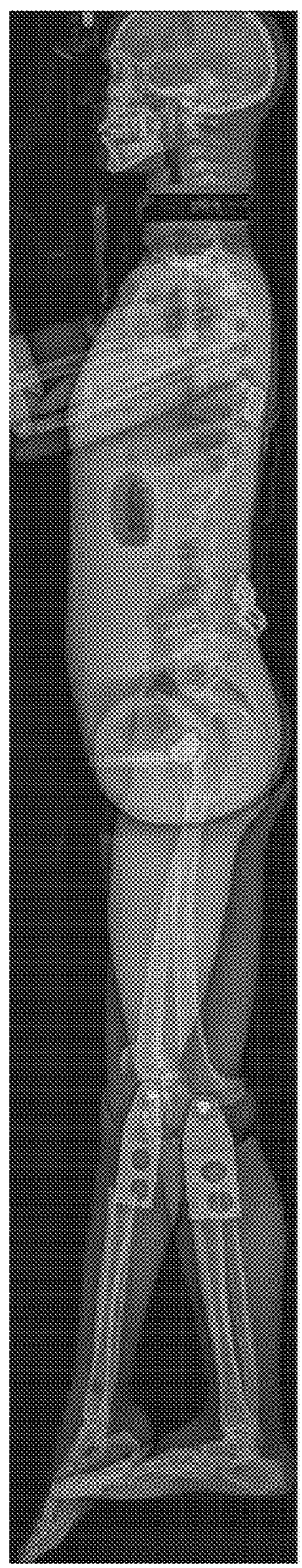
FIG. 19 shows an example of final lateral image as displayed to the radiologist.

FIG. 19 shows an example of final lateral image as displayed to the radiologist. The FIG. 19 presents for instance the lateral scan image acquired with voltage and current modulation including the demodulation and contrast enhancement processing as it is presented to the radiologist. This final lateral image is of very good quality.

The invention has been described with reference to preferred embodiments. However, many variations are possible within the scope of the invention.

The invention claimed is:

1. A radiological imaging method comprising:
2 radiation sources with imaging directions orthogonal to each other, one frontal radiation source and one lateral radiation source, sliding vertically so as to perform vertical scanning of a standing patient along a vertical scanning direction,
wherein said radiological method comprises at least one operating mode in which:
a frontal scout view is made by performing a preliminary vertical scanning of a standing patient along said vertical scanning direction by said frontal radiation source,
said frontal scout view is processed to identify a specific bone(s) localization within said frontal scout view,
a driving current intensity of at least said frontal radiation source is modulated along said vertical scanning direction, depending on patient thickness and on said identified specific bone(s) localization along said vertical scanning direction,
a driving voltage intensity of said frontal radiation source is modulated along said vertical scanning direction, depending on patient thickness and on said identified specific bone(s) localization along said vertical scanning direction,
both driving current intensity and voltage intensity modulations of said frontal radiation source are performed simultaneously, preferably synchronously, and automatically, so as to improve a compromise between:
lowering the global radiation dose received by a patient during said vertical scanning, and
increasing the local image contrasts of said identified specific bone(s) localization at different imaging positions along said vertical scanning direction, for the frontal image.

2. A radiological imaging method comprising:
2 radiation sources with imaging directions orthogonal to each other, one frontal radiation source and one lateral radiation source, sliding vertically so as to perform vertical scanning of a standing patient along a vertical scanning direction,
wherein said radiological method comprises at least one operating mode in which:
a lateral scout view is made by performing a preliminary vertical scanning of a standing patient along said vertical scanning direction by said lateral radiation source,
said lateral scout view is processed to identify a specific bone(s) localization within said lateral scout view,
a driving current intensity of at least said lateral radiation source is modulated along said vertical scanning direction, depending on patient thickness and on said identified specific bone(s) localization along said vertical scanning direction,
a driving voltage intensity of said lateral radiation source is modulated along said vertical scanning direction, depending on patient thickness and on said identified specific bone(s) localization along said vertical scanning direction,
both driving current intensity and voltage intensity modulations of said lateral radiation source are performed simultaneously, preferably synchronously, and automatically, so as to improve a compromise between:
lowering the global radiation dose received by a patient during said vertical scanning, and
increasing the local image contrasts of said identified specific bone(s) localization at different imaging positions along said vertical scanning direction, for the lateral image.

3. A radiological imaging method comprising:
2 radiation sources with imaging directions orthogonal to each other, one frontal radiation source and one lateral radiation source, sliding vertically so as to perform vertical scanning of a standing patient along a vertical scanning direction,
wherein said radiological method comprises at least one operating mode in which:
frontal and lateral scout views are made by performing a preliminary vertical scanning of a standing patient along said vertical scanning direction by said frontal and lateral radiation sources,
said frontal and lateral scout views are processed to identify a specific bone(s) localization within both said frontal and lateral scout views,
driving current intensities of both said frontal and lateral radiation sources are modulated along said vertical scanning direction, depending on patient thickness and on said identified specific bone(s) localization along said vertical scanning direction, driving voltage intensities of both frontal and lateral radiation sources are modulated along said vertical scanning direction, depending on patient thickness and on said identified specific bone(s) localization along said vertical scanning direction, both driving current intensity and voltage intensity modulations of said frontal radiation source, as well as both driving current intensity and voltage intensity modulations of said lateral radiation source, are all performed simultaneously, preferably synchronously, and automatically, so as to improve a compromise between:

lowering the global radiation dose received by a patient during said vertical scanning, and increasing the local image contrasts of said identified specific bone(s) localization at different imaging positions along said vertical scanning direction, for the frontal image and for the lateral image.

4. The radiological imaging method according to claim 1, wherein said both driving current intensity and voltage intensity modulations of said frontal radiation source are performed also so as to reach a value of signal to noise ratio which is constant and common to most of said imaging positions along said vertical scanning direction, preferably to all said imaging positions along said vertical scanning direction, for said frontal image and/or for said lateral image, but which can take two different values respectively for frontal image and for lateral image.

5. The radiological imaging method according to claim 4, wherein, for each of said frontal and/or lateral images, said signal to noise ratio value is constant and predetermined for each different patient organ to be imaged.

6. The radiological imaging method according to claim 4, wherein:

for a frontal image of a patient spine, said standard signal to noise ratio value corresponds to a number of X-ray photons received per detector pixel comprised between 50 and 70, the radiological imaging method operator preferably having the possibility to deviate, via a manual command, from this standard value by at least + or −20%, more preferably by at least + or −50%, and/or for a lateral image of a patient spine, said standard signal to noise ratio value corresponds to a number of X-ray photons received per detector pixel comprised between 20 and 40, the radiological imaging method operator preferably having the possibility to deviate, via a manual command, from this standard value by at least + or −20%, more preferably by at least + or −50%.

7. The radiological imaging method according to claim 1, wherein said frontal and/or lateral image, after having undergone at least a first step of increasing the local image contrasts of said identified specific bone(s) localization at different imaging positions along said vertical scanning direction, is normalized by homogenization of regions located just outside patient body contours, in order to get rid of image artifacts coming from said driving current intensity and voltage intensity modulations.

8. The radiological imaging method according to claim 7, wherein said frontal and/or lateral image, after having been normalized, undergoes a contrast enhancement step.

9. The radiological imaging method according to claim 1, wherein said identified specific bone(s) localization excludes metallic parts, if any, as for example metallic prosthesis of part of skeleton of patient body or as for example metallic protections put in place on patient body before performing said radiological imaging method.

10. The radiological imaging method according to claim 1, wherein:

modulations of both current intensity and voltage intensity:

simultaneously increase both current intensity and voltage intensity for bigger patient thicknesses, simultaneously decrease both current intensity and voltage intensity for smaller patient thicknesses, current intensity variation rate being slower than voltage intensity variation rate.

11. The radiological imaging method according to claim 1, wherein said current intensity modulation is maximized so as to also maximize said vertical scanning speed at a constant value.

12. The radiological imaging method according to claim 1, wherein said operating mode can be either switched on or switched off manually by a radiological imaging method operator.

13. The radiological imaging method according to claim 1, wherein said current intensity modulation(s) rate do(es) not go beyond a predetermined threshold of 5 mA per millisecond, preferably a predetermined threshold of 2 mA per millisecond, more preferably a predetermined threshold of 1 mA per millisecond.

14. The radiological imaging method according to claim 1, wherein said current intensity modulation(s) at least range(s) from 20 mA to 300 mA, and preferably from 10 mA to 400 mA.

15. The radiological imaging method according to claim 1, wherein said voltage intensity modulation(s) at least range(s) from 60 kV to 100 kV, and preferably from 50 kV to 120 kV.

16. The radiological imaging method according to claim 1, wherein said vertical scanning speed value at least range(s) from 8 cm/second to 20 cm/second, and preferably from 4 cm/second to 30 cm/second.

17. The radiological imaging method according to claim 1, wherein each of said frontal and/or lateral scout view(s) is made by performing a preliminary vertical scanning of a standing patient along a vertical scanning direction with a reduced global radiation dose as compared to each of said frontal and lateral images, before making each of said frontal and lateral images.

18. The radiological imaging method according to claim 16, wherein said reduced global radiation is less than 10% of said global radiation dose, preferably less than 5% of said global radiation dose.

19. The radiological imaging method according to claim 1, wherein pixels in said scout view are gathered together, preferably by zones of N×N pixels, more preferably by zones of at least 10×10 pixels, to make imaged zones.

20. The radiological imaging method according to claim 1, wherein said images or said imaged zones are processed to identify salient points which in turn are used to compute said thickness profile and to identify said specific bone(s) localization of a standing patient along said vertical scanning direction.

21. The radiological imaging method according to claim 1, wherein said images or said imaged zones are processed by a neural network to compute said thickness profile and to identify said specific bone(s) localization of a standing patient along said vertical scanning direction.

22. The radiological imaging method according to claim 1, wherein said 2 radiation sources slide vertically so as to perform vertical scanning of a pelvis or of rachis or of a spine or of a full body of a standing patient along a vertical scanning direction.

23. The radiological imaging method according to claim 1, wherein 2 radiation detectors are respectively associated with said 2 radiations sources, said 2 radiation detectors being 2 Photon Counting Detectors (PCD) each being associated to an automatic image processing function balancing automatically image density whatever radiation dose received on the sensitive surface of said radiation detector to enhance image contrast.

24. The radiological imaging method according to claim 1, wherein 2 radiation detectors are respectively associated with said 2 radiations sources, said 2 radiation detectors being 2 multi-energy counting detectors, preferably being 2 Energy Resolved Photon Counting Detectors (ERPCD).

* * * * *